(12) United States Patent
Routenberg

(10) Patent No.: US 9,012,374 B2
(45) Date of Patent: *Apr. 21, 2015

(54) METHODS FOR MANUFACTURING MOLECULAR ARRAYS

(71) Applicant: Prognosys Biosciences, Inc., La Jolla, CA (US)

(72) Inventor: David A. Routenberg, San Diego, CA (US)

(73) Assignee: Prognosys Biosciences, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/692,250

(22) Filed: Dec. 3, 2012

(65) Prior Publication Data

US 2013/0096033 A1    Apr. 18, 2013

Related U.S. Application Data

(63) Continuation of application No. 13/283,906, filed on Oct. 28, 2011.

(51) Int. Cl.
| | | |
|---|---|---|
| C40B 50/18 | (2006.01) | |
| C40B 40/06 | (2006.01) | |
| C40B 50/06 | (2006.01) | |
| B01J 19/00 | (2006.01) | |
| C40B 60/12 | (2006.01) | |

(52) U.S. Cl.
CPC ............ *C40B 50/06* (2013.01); *B01J 19/0046* (2013.01); *C40B 40/06* (2013.01); *C40B 60/12* (2013.01); *C40B 50/18* (2013.01); *B01J 2219/00317* (2013.01); *B01J 2219/00382* (2013.01); *B01J 2219/00585* (2013.01); *B01J 2219/00619* (2013.01); *B01J 2219/00722* (2013.01); *B01J 2219/00725* (2013.01)

(58) Field of Classification Search
None
See application file for complete search history.

(56) References Cited

U.S. PATENT DOCUMENTS

| | | | |
|---|---|---|---|
| 6,210,894 | B1 | 4/2001 | Brennan |
| 6,485,982 | B1 | 11/2002 | Charlton |
| 6,565,813 | B1 | 5/2003 | Garyantes |
| 6,632,641 | B1 | 10/2003 | Brennan et al. |
| 6,800,453 | B2 | 10/2004 | Labaer et al. |
| 7,544,473 | B2 | 6/2009 | Brenner |
| 7,674,752 | B2 | 3/2010 | He et al. |

(Continued)

FOREIGN PATENT DOCUMENTS

| | | |
|---|---|---|
| WO | WO 2008/155585 | 12/2008 |
| WO | WO 2010100265 A1 * | 9/2010 |
| WO | WO-2013/063365 | 5/2013 |

OTHER PUBLICATIONS

Leamon et al. (Electrophoresis, 2003, 24:3769-3777).*

(Continued)

*Primary Examiner* — Ardin Marschel
*Assistant Examiner* — Jeremy C Flinders
(74) *Attorney, Agent, or Firm* — Morrison & Foerster LLP

(57) ABSTRACT

The methods of the present invention provide methods for manufacturing a master substrate and methods for manufacturing replica arrays from the master substrate. The methods may be used, for example, directly to manufacture or "print" peptide arrays from a DNA array; however, the methods are applicable to a wide range of manufacturing applications for use any time multiple copies of an array needs to be printed.

18 Claims, 12 Drawing Sheets

(56) References Cited

U.S. PATENT DOCUMENTS

| | | |
|---|---|---|
| 2003/0232382 A1 | 12/2003 | Brennan et al. |
| 2005/0048580 A1 | 3/2005 | Labaer et al. |
| 2005/0260653 A1 | 11/2005 | Labaer et al. |
| 2008/0071071 A1 | 3/2008 | LaBaer et al. |
| 2008/0293591 A1 | 11/2008 | Taussig et al. |
| 2008/0312103 A1 | 12/2008 | Nemoto et al. |
| 2010/0041046 A1 | 2/2010 | Chiu et al. |
| 2011/0052446 A1* | 3/2011 | Hirano et al. ............... 422/68.1 |
| 2011/0077172 A1 | 3/2011 | Aizenberg et al. |
| 2012/0015844 A1 | 1/2012 | Zengerle et al. |
| 2013/0109595 A1 | 5/2013 | Routenberg |

OTHER PUBLICATIONS

Darhuber et al. (J. Appl. Phys., 2000, 88(9):5119-5126).*
Reynolds et al. (Journal of Colloidal and Interface Science, 2010, 352:202-210).*
International Search Report for PCT/US12/62071, (Jan. 2013).
Angenendt, et al., "Cell-free expression and functional assay in a nanowell chip format," Analytical Chemistry, 76(7):1844-49 (2004).
Angenendt, et al., "Generation of High Denisty Protein Microarrays by Cell-free in Situ Expression of Unpurified PCR Products," *Molecular and Cellular Proteomics*, Chapter 5.9, pp. 1658-1666 (2006).
Burns, et al., "Well-less, gel-permeation formats for ultra-HTS," DDT, 6(12):S40-S47 (2001).
Carlson, et al., "Formylglycine-generating Enzyme," J. of Biological Chemistry, 283(29):20117-125 (2008).
Chandra, et al., "Cell-free synthesis-based protein microarrays and their applications," Proteomics ePub, 5(6):717-30 (2009).
Chatterjee, et al., "Microarray System," PLos One, 3(9):e3265 (2008).
Doms, et al., "Hydrophobic coatings for MEMS applications," J. of Micromechanics and Microengineering, 18(5):055030 (2008).
Dorrer and Ruhe, "Wetting of silicon nanograss: from superhydrophilic to superhydrophobic sufaces," Advanced Materials, 20_159-3 (2008).
He, et al., "In situ synthesis of protein arrays," Current Opinion in Biotechnology, 19:4-9 (2008).
He, et al., "In situ synthesis of protein arrays," Current Opinion in Biotechnology, 19:4-9 (2008) Supplementary figures.
He, "Cell-free protein synthesis: applications in proteomics and biotechnology," New Biotechnology, 25(2/3):126-32 (2008).
He, et al., "Printing protein arrays from DNA arrays," Nature Methods, 5:175-77 (2008).
Hong and Pan, "Surface microfluidics fabricated by photopatternable superhydrophobic nancomposite," Microfluidics and Nanofluidics, 10(5):991-97 (2010).
Ishii, et al., "Micro Droplet Transfer between Superhydrophobic Surfaces via a High Adhesive Superhydrophobic Surface", BIOSTEC 2009, CCIS 52:136-42 (2010).
Jokinen, et al., "Complex Droplets on Chemically Modified Silicon Nanograss," Advanced Materials, 20(18):3453-56 (2008).
Kobayashi, et al., "Formation of superhydrophilic/superhydrophobic patterns by combination of nanostructureimprinted perfluoropolymer and nanostructured silicon oxide for biological droplet generation," Applied Physics Letters, 98:123706 (2011).
Kobayashi, et al., "Novel combination of hydrophilic/hydrophobic surface for large wettability difference and its application to liquid manipulation," Lab Chip, 11 (4):639-44 (201 0).
Kollias, et al., "Production of a superhydrophilic surface by aluminum-induced crystallization of amorphous silicon," Nanotechnology, 19(46):465304 (2008).
Kung, et al. , "A capillary pumping device utilizing super-hydrophobic silicon grass," J. of Micromechanics and Microengineering, 21 (6):065009 (2011).
Leng, et al., "Agarose droplet microfluidics for highly parallel and efficient single molecule emulsion PCR," Lab Chip 10(21):2841-43 (2010).
Liberski, et al., "One cell-one well: a new approach to inkjet printing single cell microarrays," ACS Comb Sci, 13:190-95 (2010).
Nand, et al., "Emerging technology of in situ cell free expression protein microarrays", Protein Cell, 3(2):84-88 (2012).
Niemeyer, "The developments of semisynthetic DNA/protein conjugates," Trends Biotechnol, 20(9):395-401(2002).
Piret, et al., "Biomolecule and nanoparticle transfer on patterned and heterogeneously wetted superhydrophobic silicon nanowire surfaces," Langmuir, 24:1670-72 (2008).
Ramachandran et al., Next-generation high-density self-assembling functional protein arrays,: Nature Methods, 5(6):535-38 (2008).
Sainiemi, et al., "Non-Reflecting Silicon and Polymer Surfaces by Plasma Etching and Replication," Advanced Materials 23:122-26 (2011).
Sakaihara, et al., "A single-molecule enzymatic assay in a directly accessible femtoliter droplet array," Lab Chip 10:3355-62 (201 0).
Sasuga et al., "Single-cell chemicalltsis method for analyses of intracellular molecules using an array of picoliter-scale microwells," Analyticial hemistry, 80(23):9141-49 (2008).
Stoevesandt et al., New Biotechnology, 2010, 28(3):282-290.
Stoevesandt, et al., "Protein arraying by cell-free expression and diffusion across a fluid-filled gap", New Biotechnology, 29(5):586-88 (2012).
Stoevesandt, et al., "Producing Protein Microarrays from DNA MicroarraXs", Chapter 18 in Protein Microaarys: Methods and Protocols, Methods in Molecular Biology, vol. 785 Springer Science+Business Media) (2011).
Takulapalli, et al., "High Density Diffusion-Free Nanowell Arrays", J. of Proteome, pre-print dx.doi.org/1 0.1 021/pr300 67q, (2012).
Teshima, et al., "Uitrahydrophobic/Uitrahydrophilic, Micropatterning on a Polymeric Substrate," 11 (8-9):347-49 (2005).
Teshimi et al., Chem. Vap. Deposition, 2005, 11:347-349.
Tolbert and Wong, "New Methods for Proteomic Research: Preparation of Proteins with N-Terminal Cysteines for Labeling and Conjugation," Angew. Chern, Int. Ed., 41 (2):2171-74 (2002).
Restriction Requirement for U.S. Appl. No. 13/283,906, mailed Feb. 15, 2012, 7 pages.
Response to Restriction Requirement for U.S. Appl. No. 13/283,906, dated Mar. 9, 2012, 4 pages.
Office Action for U.S. Appl. No. 13/283,906, mailed Apr. 11, 2012, 16 pages.
Response to Office Action for U.S. Appl. No. 13/283,906, filed May 8, 2012, 13 pages.
Final Office Action for U.S. Appl. No. 13/283,906, mailed Jun. 14, 2012, 25 pages.
Response to Final Office Action for U.S. Appl. No. 13/283,906, filed Jul. 27, 2012, 16 pages.
Advisory Action for U.S. Appl. No. 13/283,906, mailed Aug. 17, 2012, 4 pages.
Request for Continued Examination for U.S. Appl. No. 13/283,906, filed Sep. 11, 2012, 3 pages.
Supplemental Response and Preliminary Amendment for U.S. Appl. No. 13/283,906, filed Dec. 3, 2012, 4 pages.
Office Action for U.S. Appl. No. 13/283,906, mailed Mar. 13, 2013, 7 pages.
Response to Office Action for U.S. Appl. No. 13/283,906, filed Aug. 6, 2013, 12 pages.
Final Office Action for U.S. Appl. No. 13/283,906, mailed Sep. 11, 2013, 10 pages.
Response to Final Office Action for U.S. Appl. No. 13/283,906, filed Oct. 25, 2013, 15 pages.
Advisory Action for U.S. Appl. No. 13/283,906, mailed Nov. 4, 2013, 3 pages.
Office Action for U.S. Appl. No. 13/283,906, mailed Nov. 27, 2013, 10 pages.
Response to Office Action for U.S. Appl. No. 13/283,906, filed Feb. 24, 2014.
International Preliminary Report on Patentability and Written Opinion for PCT/US2012/062071, issued Apr. 29, 2014, 6 pages.

* cited by examiner

METHODS FOR MANUFACTURING MOLECULAR ARRAYS

RELATED APPLICATIONS

This application is a continuation of U.S. Ser. No. 13/283,906, filed Oct. 28, 2011.

This invention was made with the support of the Federal Government under Grant No. R44RR025296. The Federal Government has certain rights in this invention.

FIELD OF THE INVENTION

This invention relates to methods for manufacturing molecular arrays.

BACKGROUND OF THE INVENTION

In the following discussion certain articles and methods may be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Molecular arrays typically are precisely-ordered arrangements of large sets of nucleic acid, protein or other molecules immobilized on solid substrates, and are valuable tools in areas of research that require the identification and/or quantification of many molecules in parallel. DNA arrays are the most common type of molecular arrays and have been used in genetic mapping studies, mutational analyses and in genome-wide monitoring of gene expression and have become standard tools in research, diagnostic and clinical applications. Molecular arrays of proteins or peptides are increasingly used in the art and are particularly useful in high throughput screening of molecular interactions such as protein-protein binding and enzymatic activities.

Traditionally, peptide arrays have been made by spotting pre-synthesized peptides on a surface (Salisbury, et al., J. Am. Chem. Soc. 124(50):14868-70 (2002)) or by synthesizing peptides in spots on cellulose filter sheets using standard solid phase peptide synthesis (known as the SPOT method, see Frank, J. Immunol. Methods, 267(1):13-26 (2002)). However, the cost of generating arrays with tens of thousands or more spotted peptides would be astronomically high. Several methods enable direct chemical synthesis of peptides in microarray format, which reduces costs, but these methods still have the major drawback of variability in the quality of the synthesized peptides (Antohe and Cooley, Methods Mol. Biol., 381:299-312 (2007)). Moreover, the direct fabrication process can be very slow and inefficient (Hilpert, et al., Nat. Protoc., 2:1333-49 (2007)).

Recently, methods for peptide array fabrication by in vitro translation of arrayed nucleic acids have been developed, including protein in situ array (PISA) production (He and Taussig, Nucleic Acids Res., 29: e73 (2001)), nucleic acid programmable protein array (NAPPA) production (Ranachandran, et al., Science, 305:86-90 (2004)), DNA to protein array (DAPA) construction (He, Nat. Methods, 5:175-177 (2008)), and arraying of proteins using in situ puromycin capture (Tao and Zhu, Nat. Biotech, 24:1253-1254 (2006)). These approaches utilize individually-synthesized nucleic acid templates rather than individually-synthesized peptides; however, the cost of the nucleic acid templates is often higher than the cost of individual peptides arrayed by traditional methods. Further, diffusion of the peptide products limits the feature density of these types of arrays.

The ability to manufacture large, high-quality, sequence-diverse molecular arrays in a cost effective manner would be of great benefit generally in molecular research, and in the development of diagnostics and therapeutics in particular. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the written Detailed Description including those aspects illustrated in the accompanying drawings and defined in the appended claims.

The present invention thus provides in some embodiments a method of manufacturing an array of products on a substrate comprising providing partitioned reaction volumes on the substrate, where the partitioned reaction volumes are partitioned by surface energetic barriers; generating products by one or more enzymatic processes in the partitioned reaction volumes; and immobilizing the products from the partitioned reaction volumes on capture moieties on the substrate, where partitioning between products from separate partitioned reaction volumes is preserved.

In some aspects of this embodiment there are at least 100 or more partitioned reaction volumes per square centimeter on the substrate. In other aspects of this embodiment, there are at least 250, 500, 750, 1000 or more partitioned reaction volumes per square centimeter on the substrate. In yet other embodiments, there are at least 1250, 1500, 1750, 2000, 2500, 3000, 4000, 5000, 7500, 10,000 or more partitioned reaction volumes per square centimeter on the substrate. In additional embodiments, there are at least 12,500, 15,000, 17,500, 20,000, 25,000, 30,000, 40,000, 50,000, 75,000, 100,000 or more partitioned reaction volumes per square centimeter on the substrate.

In some aspects of this embodiment there are at least 100 or more features per square centimeter comprising reaction products captured on the substrate. In other aspects of this embodiment, there are at least 250, 500, 750, 1000 or more features per square centimeter comprising reaction products captured on the substrate. In yet other embodiments, there are at least 1250, 1500, 1750, 2000, 2500, 3000, 4000, 5000, 7500, 10,000 or more features per square centimeter comprising reaction products captured on the substrate. In additional embodiments, there are at least 12,500, 15,000, 17,500, 20,000, 25,000, 30,000, 40,000, 50,000, 75,000, 100,000 or more features per square centimeter comprising reaction products captured on the substrate.

In some aspects of this embodiment, at least 25, 50, 100, 250, 500, 1000, 2500, 5000, 10,000, 15,000, 20,000, 25,000 or more different products from separate partitioned reaction volumes are arrayed on the substrate, and in other aspects at least a portion of each product from substantially all partitioned reaction volumes are arrayed on the substrate. In additional embodiments, there are at least 30,000, 40,000, 50,000, 75,000, 100,000, 150,000, 200,000 or 300,000 or more different products from separate partitioned reaction volumes arrayed on the substrate. In yet other embodiments, there are at least 400,000, 500,000, 750,000, or 1,000,000 or more different products from separate partitioned reaction volumes arrayed on the substrate.

In some aspects of this embodiment, the surface energetic barriers are provided on the substrate. Yet other aspects of this embodiment further include a step of introducing a second substrate in proximity to the first substrate where the surface energetic barriers are provided on the second substrate.

In some aspects of this embodiment, the one or more enzymatic processes comprise one or more of replication, transcription or translation, and in yet other embodiments, the one or more enzymatic processes comprise both transcription and translation. In some aspects, the substrate comprises template molecules, where the template molecules comprise nucleic acids, and the products comprise nucleic acids or proteins. In some aspects, the one or more enzymatic processes utilize one or more polymerases.

An additional embodiment of the invention includes a method of manufacturing an array of products on a replica array comprising providing a master substrate having partitioned reaction volumes; generating products by one or more enzymatic processes in the partitioned reaction volumes; and immobilizing the products from the partitioned reaction volumes from the master substrate on capture moieties disposed on the replica array that is in contact with the partitioned reaction volumes, where partitioning between products from separate partitioned reaction volumes is preserved.

In some aspects of this embodiment, the reaction volumes are partitioned by surface energetic barriers on the master substrate, and in some aspects the master substrate is a template array. In yet other embodiments, the reaction volumes are partitioned by surface energetic barriers on a dummy substrate.

In some aspects of this embodiment, there are at least 100 or more partitioned reaction volumes per square centimeter on the master substrate. In other aspects of this embodiment, there are at least 250, 500, 750, 1000 or more partitioned reaction volumes per square centimeter on the master substrate. In yet other embodiments, there are at least 1250, 1500, 1750, 2000, 2500, 3000, 4000, 5000, 7500, 10,000 or more partitioned reaction volumes per square centimeter on the master substrate. In additional embodiments, there are at least 12,500, 15,000, 17,500, 20,000, 25,000, 30,000, 40,000, 50,000, 75,000, 100,000 or more partitioned reaction volumes per square centimeter on the master substrate.

In some aspects of this embodiment there are at least 100 or more features per square centimeter comprising reaction products captured on the replica array. In other aspects of this embodiment, there are at least 250, 500, 750, 1000 or more features per square centimeter comprising reaction products captured on the replica array. In yet other embodiments, there are at least 1250, 1500, 1750, 2000, 2500, 3000, 4000, 5000, 7500, 10,000 or more features per square centimeter comprising reaction products captured on the replica array. In additional embodiments, there are at least 12,500, 15,000, 17,500, 20,000, 25,000, 30,000, 40,000, 50,000, 75,000, 100,000 or more features per square centimeter comprising reaction products captured on the replica array.

In some aspects of this embodiment, at least 25, 50, 100, 250, 500, 1000, 2500, 5000, 10,000, 15,000, 20,000, 25,000 or more different products from separate partitioned reaction volumes are arrayed on the replica array, and in other aspects at least a portion of each product from substantially all partitioned reaction volumes are arrayed on the replica array. In additional embodiments, there are at least 30,000, 40,000, 50,000, 75,000, 100,000, 150,000, 200,000 or 300,000 or more different products from separate partitioned reaction volumes arrayed on the replica array. In yet other embodiments, there are at least 400,000, 500,000, 750,000, or 1,000,000 or more different products from separate partitioned reaction volumes arrayed on the replica array.

In some aspects of this embodiment, the method further includes after the immobilizing step, the steps of removing the replica array; sequentially furnishing one or more additional replica arrays comprising capture moieties; and immobilizing the products from the partitioned reaction volumes from the master substrate on the capture moieties on the one or more additional replica arrays, where partitioning between products from separate partitioned reaction volumes is preserved.

In some aspects of this embodiment, the method is used to manufacture 2, 3, 4, 5, 10, 20 or more arrays of products on replica arrays using a single master substrate. In other embodiments, at least 30, 40, 50, 75, 100, 200, 300 or more arrays of products on replica arrays are manufactured using a single master substrate. In still other embodiments, 400, 500, 750, 1000 or more arrays of products on replica arrays are manufactured from a single master substrate.

In yet other aspects of this embodiment, the method further includes after the immobilizing step, the additional steps of replenishing or regenerating partitioned reaction volumes on the master substrate; generating products by one or more enzymatic processes in the partitioned reaction volumes on the master substrate; sequentially furnishing one or more additional replica arrays comprising capture moieties; and immobilizing the products from the partitioned reaction volumes from the master substrate on the capture moieties on the one or more additional replica arrays, wherein partitioning between products from separate partitioned reaction volumes is preserved.

In some aspects of this embodiment, at least one component of the enzymatic reaction is attached to the master substrate. Also, in some aspects of this embodiment, the one or more enzymatic processes comprise one or more of replication, transcription or translation, and in yet other embodiments, the one or more enzymatic processes comprises both transcription and translation. In some aspects, the one or more enzymatic processes utilize one or more polymerases.

Other embodiments of the invention provide a method of manufacturing an array of products on a replica array comprising providing a template array comprising template molecules, a master substrate, and partitioned reaction volumes that are located between the template array and the master substrate; generating products by one or more enzymatic processes from the template molecules on the template array in the partitioned reaction volumes; separating the template array from the master substrate, retaining the partitioned reaction volumes on the master substrate; bringing a replica array into contact with the partitioned reaction volumes; and immobilizing the products from the partitioned reaction volumes on capture moieties disposed on the replica array, wherein partitioning between products from separate partitioned reaction volumes is preserved.

In some aspects of these embodiments, the reaction volumes are partitioned by surface energetic barriers. In some aspects, the surface energetic barriers are located on one or more of the template array, the master substrate, the replica array or a dummy substrate.

In some aspects of this embodiment, there are at least 100 or more partitioned reaction volumes per square centimeter on the master substrate. In other aspects of this embodiment, there are at least 250, 500, 750, 1000 or more partitioned reaction volumes per square centimeter on the master substrate. In yet other embodiments, there are at least 1250, 1500, 1750, 2000, 2500, 3000, 4000, 5000, 7500, 10,000 or more partitioned reaction volumes per square centimeter on the master substrate. In additional embodiments, there are at least 12,500, 15,000, 17,500, 20,000, 25,000, 30,000, 40,000, 50,000, 75,000, 100,000 or more partitioned reaction volumes per square centimeter on the master substrate.

In some aspects of this embodiment there are at least 100 or more features per square centimeter comprising reaction products captured on the replica array. In other aspects of this embodiment, there are at least 250, 500, 750, 1000 or more features per square centimeter comprising reaction products captured on the replica array. In yet other embodiments, there are at least 1250, 1500, 1750, 2000, 2500, 3000, 4000, 5000, 7500, 10,000 or more features per square centimeter comprising reaction products captured on the replica array. In additional embodiments, there are at least 12,500, 15,000, 17,500, 20,000, 25,000, 30,000, 40,000, 50,000, 75,000, 100,000 or more features per square centimeter comprising reaction products captured on the replica array.

In some aspects of this embodiment, at least 25, 50, 100, 250, 500, 1000, 2500, 5000, 10,000, 15,000, 20,000, 25,000 or more different products from separate partitioned reaction volumes are arrayed on the replica array, and in other aspects at least a portion of each product from substantially all partitioned reaction volumes are arrayed on the replica array. In additional embodiments, there are at least 30,000, 40,000, 50,000, 75,000, 100,000, 150,000, 200,000 or 300,000 or more different products from separate partitioned reaction volumes arrayed on the replica array. In yet other embodiments, there are at least 400,000, 500,000, 750,000, or 1,000,000 or more different products from separate partitioned reaction volumes arrayed on the replica array.

In some aspects of this embodiment, the method further includes after the immobilizing step, the steps of removing the replica array; sequentially furnishing one or more additional replica arrays comprising capture moieties; and immobilizing the products from the partitioned reaction volumes from the master substrate on the capture moieties on the one or more additional replica arrays, where partitioning between products from separate partitioned reaction volumes is preserved.

In some aspects of this embodiment, the method is used to manufacture 2, 3, 4, 5, 10, 20 or more arrays of products on replica arrays using a single master substrate. In other embodiments, at least 30, 40, 50, 75, 100, 200, 300 or more arrays of products on replica arrays are manufactured using a single master substrate. In still other embodiments, 400, 500, 750, 1000 or more replica arrays of products on replica arrays are manufactured from a single master substrate.

In yet other aspects of this embodiment, the method further includes after the immobilizing step, the additional steps of replenishing or regenerating partitioned reaction volumes on the master substrate; generating products by one or more enzymatic processes in the partitioned reaction volumes on the master substrate; sequentially furnishing one or additional more replica arrays comprising capture moieties; and immobilizing the products from the partitioned reaction volumes from the master substrate on the capture moieties on the one or more additional replica arrays, wherein partitioning between products from separate partitioned reaction volumes is preserved.

In some aspects of this embodiment, the one or more enzymatic processes comprise one or more of replication, transcription or translation, and in yet other embodiments, the one or more enzymatic processes comprises both transcription and translation. In some aspects, the one or more enzymatic processes utilize one or more polymerases.

Other embodiments of the invention provide a protein array comprising at least 50,000 unique enzymatically generated protein products at a density of at least 10,000 features per square centimeter.

In some aspects of this embodiment, at least 10,000, 20,000, 25,000, 40,000 or more unique enzymatically generated protein products are provided, and in yet other aspects, at least 75,000, 100,000, 200,000, 250,000, 500,000, 1,000,000 or more unique enzymatically generated protein products are provided on the protein array. In some aspects unique protein products are provided at a density of at least 100, 250, 500, 750, 1000, 1250, 2000, 2500, 3000, 4000, 5000, 7500, 10,000 or more features per square centimeter, and in yet other aspects, unique protein products are provided at a density of at least 12,500, 15,000, 20,000, 25,000, 30,000, 40,000, 50,000, 75,000, 100,000 or more features per square centimeter on the protein array.

These and other methods for manufacturing and copying molecular arrays are described in more detail herein.

Figure 1A:
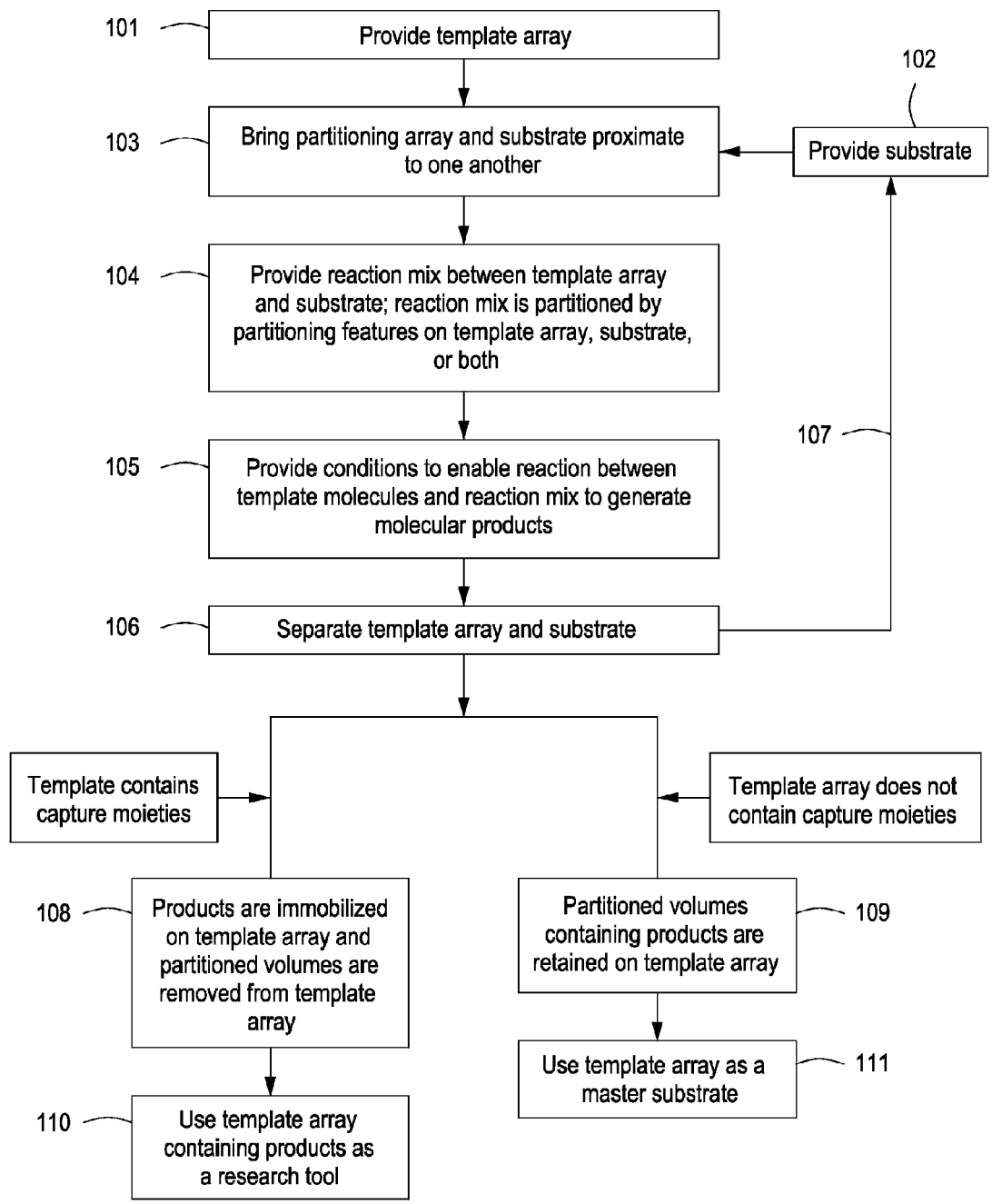
FIGS. 1A through 1D illustrate simplified methods for manufacturing molecular arrays according to the invention.

It should be noted that the features of the various molecular arrays, including substrate surfaces, substrate features, droplets and the like are not drawn to scale; rather, the features are presented in a representational manner.

DEFINITIONS

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "antibody" as used herein is intended to refer to an entire immunoglobulin or antibody or any functional fragment of an immunoglobulin molecule that is capable of specific binding to an antigen (antibodies and antigens are "binding partners" as defined herein). Examples of such peptides include complete antibody molecules, antibody fragments, such as Fab, F(ab')2, CDRS, VL, VH, and any other portion of an antibody that is capable of specifically binding to an antigen. Antibodies to be used as capture moieties in the invention are immunoreactive or immunospecific for, and therefore specifically and selectively bind to, protein products printed or copied according to the invention.

An "array" is a group of at least two features on a substrate, and an array may contain any number of features. The features may be molecular features in the case of a molecular array, or partitioning features in the case of a "partitioning array." A molecular array is called a "template array" if it contains molecules (or cells, organelles, or viruses that comprise molecules) that are used as a template for a biochemical reaction such as PCR, RT-PCR, transcription, or translation. Such molecules are called "template molecules", where such template molecules are, in preferred embodiments, directly or indirectly, covalently or non-covalently bound to the template array.

The term "binding pair" means any two molecules that are known to selectively bind to one another. In the case of two proteins, the molecules selectively bind to one another as described in more detail herein. Such binding may include covalent and/or non-covalent binding. Examples include, but are not limited to, biotin and avidin; biotin and streptavidin; an antibody and its particular epitope; and the like. A "binding scaffold" refers to binding proteins generated via combinatorial engineering and that are useful as capture moieties in certain embodiments.

The term "capture moiety" refers to any moiety that allows capture of a molecular product generated by a reaction. A substrate with capture moieties disposed thereon is termed a capture substrate where the capture moieties may be uniformly disposed or disposed as capture features. A capture substrate is called a "replica array" if, in addition to being capable of physically or chemically binding the products of a biochemical reaction involving the template molecules of a template array, it is an array product that is "printed" or "copied" or "stamped out" from a master substrate.

The term "copying" or "printing" or "stamping out" in reference to a molecular array means transferring a portion of molecular products from a master substrate (which may be a template array and/or partitioning array) to a replica array.

A "feature" is an isolated region of patterned molecules or material, or an isolated depression or relief on a substrate. Features may range in size from several millimeters down to the nanometer scale depending on the nature of the feature and the patterning technique. The areas in between features are referred to herein as "interstices", or "interstitial regions." Features may include but are not limited to isolated areas of molecules bound to or disposed upon the substrate (molecular features), and patterned regions of surface coatings such as metal, polymer, semiconductors or insulators, regions whose surface energy is markedly different from that of the interstitial region (i.e., hydrophilic features on a hydrophobic substrate). Features may also be provisions for separating a liquid into a plurality of compartments (i.e., separate droplets) where each compartment shall be referred to as a partition, and where a substrate comprising such compartments shall be referred to as "partitioned." Liquid that has been separated into drops is described as being partitioned and a reaction in such a liquid is a partitioned reaction. A feature that is employed for the purpose of producing partitions in a liquid or reaction will be referred to as a "partitioning feature." The term partitioning feature may include the feature as well as the immediately surrounding interstitial region if the properties of the interstitial region contribute to forming the partitions.

An array that is used to transform blank replica arrays into printed replica arrays is called a "master substrate."

The term "oligonucleotide" is used herein to mean a linear polymer of nucleotide monomers. As used herein, the term may refer to single-stranded or double-stranded forms. Monomers making up nucleic acids and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g., naturally occurring or non-naturally occurring analogs.

The terms "protein," "peptide," "polypeptide," and the like are used interchangeably herein, and refer to a polymeric form of amino acids of any length, comprising naturally-occurring or unnatural amino acids, or chemically or biochemically modified or derivatized amino acids, including polypeptides having modified peptide backbones.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selectively binds", "selective binding", "specific binding" and the like as used herein, when referring to a binding partner (e.g., protein, nucleic acid, antibody, etc.), refers to a binding reaction of two or more binding partners with sufficiently high affinity and/or complementarity to ensure selectivity or specificity under designated assay conditions. Typically, signal that is due to specific binding will be at least three times the standard deviation of the background signal.

The term "substrate" refers to a mechanical support upon which material may be disposed to provide functionality, whether mechanical, biological, optical, chemical or other functionality. A substrate may be unpatterned or patterned, partitioned or unpartitioned. Molecules on a substrate may be disposed in features or may be uniformly disposed on the substrate surface.

The term "surface energetic barrier" refers to a physical element provided by adjacent regions on a substrate having different surface energetic properties that is used to partition reaction volumes.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, sequencing technology, and micro- and nano-fabrication which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, *Biochemistry* (4th Ed.) (1995) W. H. Freeman, New York N.Y.; Gait, *Oligonucleotide Synthesis: A Practical Approach* (2002) IRL Press, London; Nelson and Cox, Lehninger, *Principles of Biochemistry* (2000) 3rd Ed., W. H. Freeman Pub., New York, N.Y.; and Berg, et al., *Biochemistry* (2002) 5th Ed., W. H. Freeman Pub., New York, N.Y., Jaeger, *Introduction to Microelectronic Fabrication* (2002) 2nd Ed., Prentice Hall, and Madou, *Fundamentals of Microfabrication* (2002) all of which are herein incorporated in their entirety by reference for all purposes.

Note that as used herein and in the appended claims, the singular forms "a," "an," and "the" include plural referents unless the context clearly dictates otherwise. Thus, for example, reference to "a construct" refers to one or more copies of such construct, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The methods of the present invention provide methods for manufacturing master substrates and methods for printing or copying one to many replica arrays from a single master substrate. The methods may be used directly to manufacture or "print" peptide arrays from a DNA array; however, the methods are applicable to a wide range of manufacturing applications for use any time multiple copies of an array of molecules is desired.

The invention provides methods for spatially partitioning biochemical or chemical reactions into regions of microliter to femtoliter or smaller volumes to avoid mixing of reaction products by diffusion, convection or turbulent mixing. Partitioning is effected by the use of a partitioning array comprising discrete partitioning features. Partitioning limits diffusion and preserves the spatial integrity of the reactions and resulting products. Droplets comprising a reaction mix may be assembled on the partitioning array alone, between a partitioning array and an unpartitioned substrate, or between two partitioning arrays by methods that are described infra. Features on the partitioning array may be separated merely by an adequate distance to prevent droplet mixing; alternatively, in preferred embodiments the features are partitioned into physical or virtual wells as described in more detail infra.

FIGS. 1A through 1D illustrate alternative simplified methods for manufacturing molecular arrays according to the invention. FIG. 1A illustrates one exemplary method 100. A first step 101 provides a template array comprising template molecules (or cells, organelles or viruses that comprise template molecules) arrayed in features. The template array may also comprise partitioning features in which case it would be a partitioning template array. In step 102, a substrate is provided. The substrate may be a partitioning array comprising partitioning features or it may merely act as a "dummy" substrate if the template array is a partitioning array. At least one of the template array and the substrate must be a partitioning array and both may be partitioning arrays. At step 103, the template array and substrate are brought into proximity with one another, and in step 104 a reaction mix is provided in the space between the template array and substrate. The reaction mix is spatially partitioned by the partitioning features on the template, substrate, or both. Alternatively, reaction mix may be applied to one or both of the partitioned template array or substrate before they are brought into proximity. At step 105 conditions are provided so as to enable a reaction between the template molecules disposed on the template array and the reaction mix, thereby generating products. At step 106, the template array and substrate are separated and the fate of the products depends on the nature of the template array, specifically whether or not the template array contains capture moieties. If the template contains capture moieties, the products will become immobilized on the surface of the template array after they are generated in step 105. In this case, the partitioned volumes are removed from the template array in step 108 and the template array has been converted into an array of products to be used as a research or diagnostic tool 110. If the template array does not contain capture moieties, the partitioned reaction products will remain in the partitioned reaction volumes and these partitions will be preserved on the template surface in step 109. The template thus has been converted into a master substrate 111, capable of being used to print replica arrays as described in more detail infra. The substrate may be reused 107 in the process with a fresh template array.

Figure 1B:
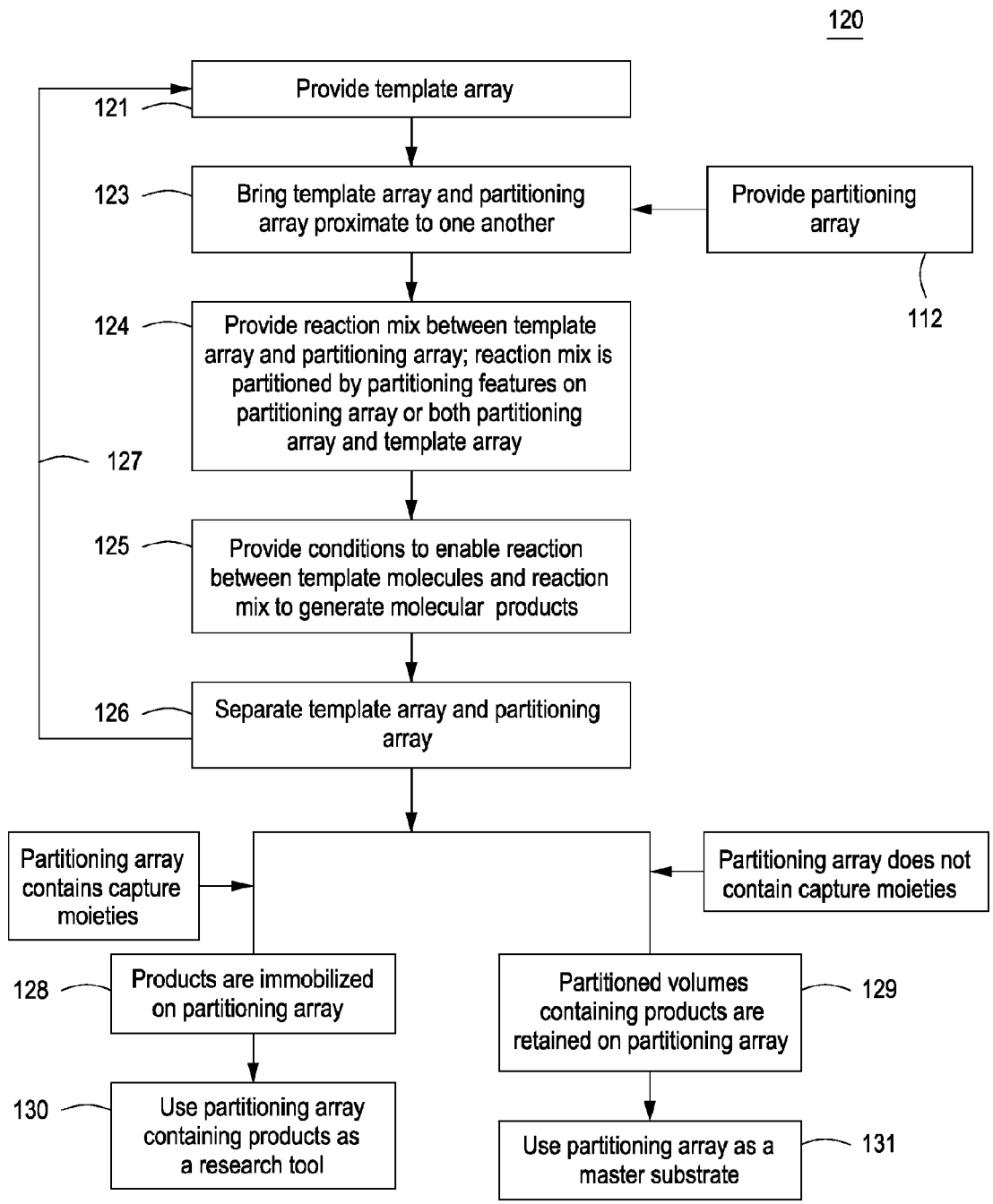

FIG. 1B illustrates an alternative exemplary method 120. In step 121, a template array with template molecules—or cells, organelles or viruses that comprise template molecules—arranged in features is provided. The template array may also comprise partitioning features. In step 122, a partitioning array is provided, where the partitioning array comprises partitioning features capable of producing partitioned reaction volumes where the arrangement of the partitioned volumes is compatible with the template molecules in features on the template array. At step 123, the template array and partitioning array are brought proximate to one another and in step 124 a reaction mix is provided in the space between the template array and partitioning array where the reaction mix is spatially partitioned by the features on the partitioning array (or the partitioning array and the template array if both comprise partitions). Again, as an alternative, reaction mix may be applied to one or both of the partitioned template array or substrate before they are brought into proximity. At step 125 conditions are provided so as to enable a reaction between the template molecules disposed on the template array and the reaction mix, thereby generating products. At step 126, the template array and partitioning array are separated and the fate of the products depends on the nature of the partitioning array, specifically whether or not the partitioning array contains capture moieties. If the partitioning array contains capture moieties, the products have become immobilized on the surface of the partitioning array after they are generated in step 125. In this case, the partitioned volumes are removed from the partitioning array in step 128 and the partitioning array thus is converted into an array of products to be used as a research or diagnostic tool 130. If the partitioning array does not contain capture moieties, the partitioned reaction products will remain in the partitioned reaction volumes and these partitions will be preserved on the partitioning array surface in step 129. The partitioning array has been converted into a master substrate 121, capable of being used to print replica arrays as described in more detail infra. The template array may be reused 127 in the array manufacturing method with a fresh partitioning array to generate more products.

Note that in the array manufacturing methods of the invention, either the template array or the substrate or both may be partitioned; that is, the combination of partitioning template array and substrate may be employed, the combination of (non-partitioning) template array and partitioning array may be employed, or the combination of partitioning template array and partitioning array may be employed. Any configuration works as long as the reaction mix is partitioned so that products produced by different template molecules reacting with the reaction mix do not mix with one another. Note also that either the template array or the partitioning array can be converted into a master substrate or a research or diagnostic tool depending on the location of the partitioning features and the presence or absence of capture moieties.

Figure 1C:
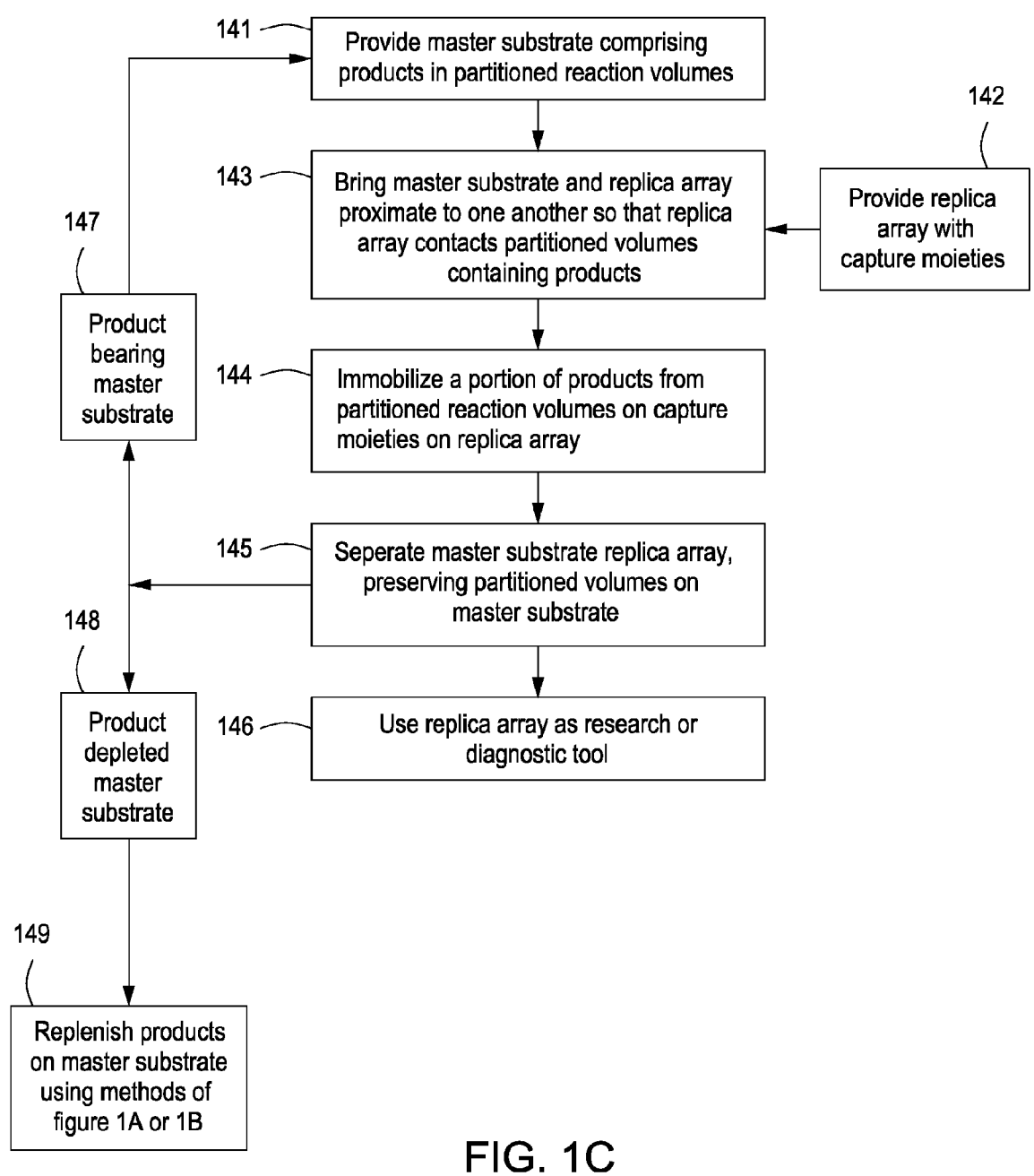

FIG. 1C illustrates yet another alternative exemplary method 140 for manufacturing, and in this embodiment printing numerous replica arrays. In a first step 141, a master substrate, comprising products in partitioned volumes is provided. The master substrate can be generated according to the methods described supra, or by other means. In step 142, a replica array is provided comprising capture moieties capable of binding the products from the master substrate. These capture moieties may be disposed in features or they may be uniformly disposed over the surface of the replica array. The replica array may but need not comprise partitioning features. At step 143, the master substrate and replica array are brought proximate to one another so that the replica array contacts the partitioned volumes on the master substrate that contain the products. In step 144 a portion of the products from the partitioned volumes is immobilized on the capture moieties of the replica array. At step 145, the master substrate and replica array are separated, preserving the partitioned volumes containing the products on the master substrate. The replica array is available to be used as a research or diagnostic tool 146. The master substrate can then be reused 147 to repeat the process at 141 as long as the partitioned volumes contain sufficient product to produce another replica array. Once the master substrate has been depleted of products, 148, the products may be replenished or regenerated by using one of the methods described in relation to FIG. 1A or FIG. 1B. Note that either the template array from FIG. 1A or the partitioning array from FIG. 1B can be used as a master substrate in FIG. 1C.

The configuration of FIG. 1B is particularly useful where the template array comprises oligonucleotides to be transcribed and translated, and a coupled transcription/translation reaction mix is used to produce peptide products from the oligonucleotides on the template array. The peptide products are retained on the partitioning array, which then acts as the master substrate to print (or copy or stamp out) one to many replica arrays depending on how quickly the peptide products on the master substrate (here, the partitioning array) are depleted. Using the partitioning array rather than the template array as the master substrate helps to preserve the integrity of the oligonucleotides (template molecules) on the template array so that the oligos can be used for repeated transcription/translation reactions to "load" products on additional partitioning arrays.

Figure 1D:
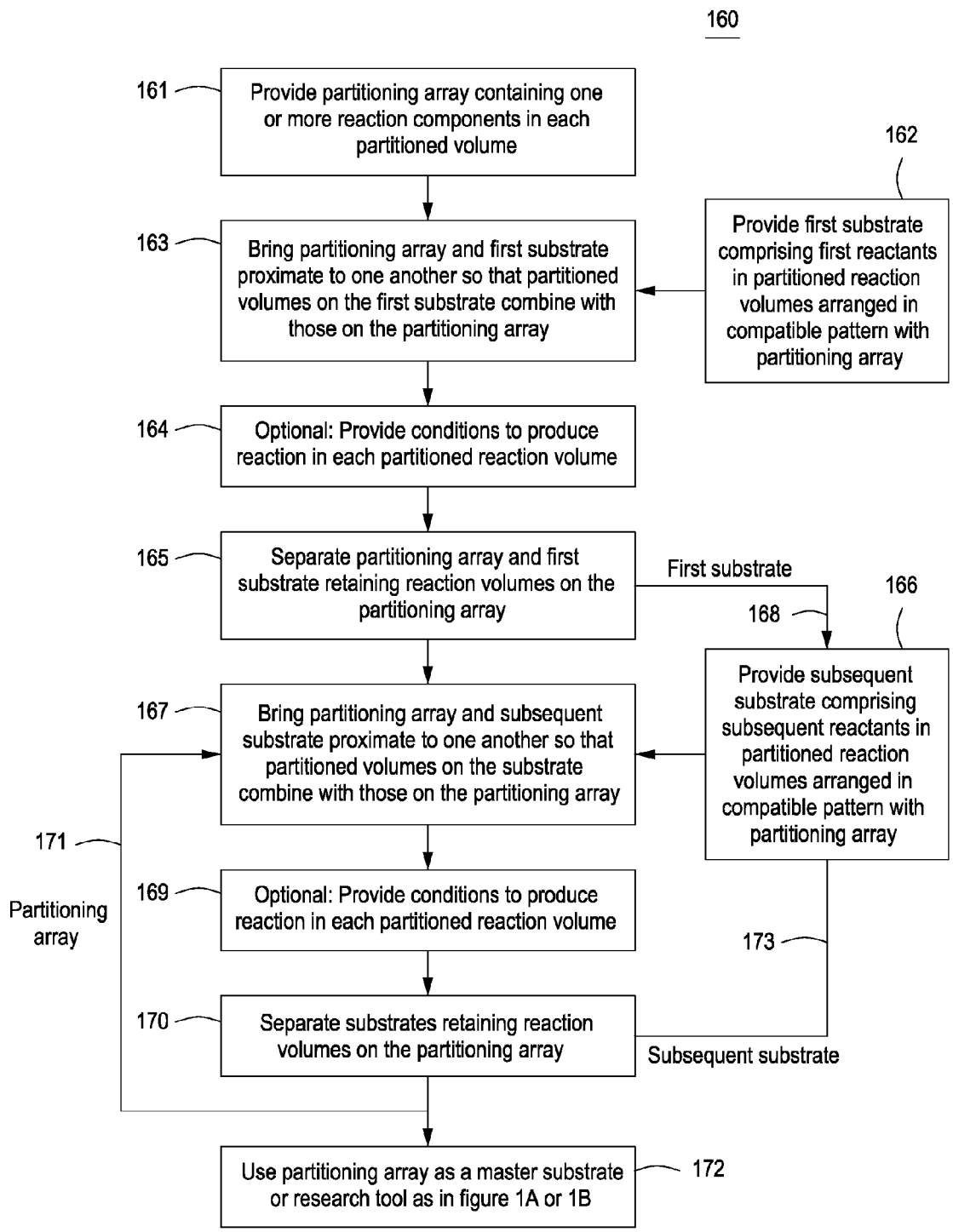

FIG. 1D illustrates another exemplary method 160 for manufacturing arrays where a series of reaction steps are performed. The embodiment illustrated in FIG. 1D allows for sequential addition of reaction components to a partitioning array, and is particularly useful to deliver enzymes (for example, peptide tag cross-linking enzymes) or other reagents that are incompatible with other reactions that take place in the sequence of reactions or for reactions that require conditions that are incompatible with other reaction conditions. In step 161, a partitioning array is provided containing one or more reaction components in each partitioned volume. This array can be generated by any of the methods described supra or by other methods. In step 162, a first substrate is provided, comprising first reactants of a chemical reaction where the reactants are also partitioned in a pattern compatible with the partitioned components on the partitioning array. At step 163 the partitioning array and first substrate are brought into proximity with one another so that the partitioned volumes on the substrate combine with those on the partitioning array. Step 164 is an optional step, wherein reaction conditions are provided to enable a reaction between the reaction components provided by the partitioning array and the first reactants provided by the first substrate. The partitioning array and substrate are separated in step 165, preserving the partitioned reaction volumes on the partitioning array.

In step 166 a subsequent substrate is provided comprising partitioned volumes of subsequent reactants (e.g., second substrate comprising second reactants, third substrate comprising third reactants, and so on) in a pattern compatible with the partitioning array. The first substrate may be recycled 168 for this step by washing and reloading with the subsequent reactants. In step 167 the substrate is brought into proximity with the partitioning array as in 163 and the partitioned volumes of subsequent reactants are combined with the partitioned volumes on the partitioning array. Again, an optional reaction step 169, providing appropriate reaction conditions, may be included. The substrate and partitioning array are separated in step 170. If the reaction requires additional components, the partitioning array is returned to step 167 for another round of loading 171. The substrate can be recycled 173 by washing and reloading with another round of subsequent reactants and reused in another cycle of 166 and 167. Once the final round of components has been added, final reaction conditions are provided 169, the substrates are separated 170, and the partitioning array is used as a master substrate or a research tool as described supra.

It should be noted that in the method 160 shown in FIG. 1D, conditions may be provided to react reaction components on the partitioning template array at any point in the process; that is, conditions may be provided after each delivery of reaction components to the partitioning template array, or at one or more but not all deliveries of reaction components to the partitioning template array. For example, at step 164 and each time through step 169 reaction conditions may be provided. Alternatively, the reaction components on the partitioning template array may not be reacted before the final iteration of step 169.

Template Molecules, Reaction Mixes and Products

Figure 2:
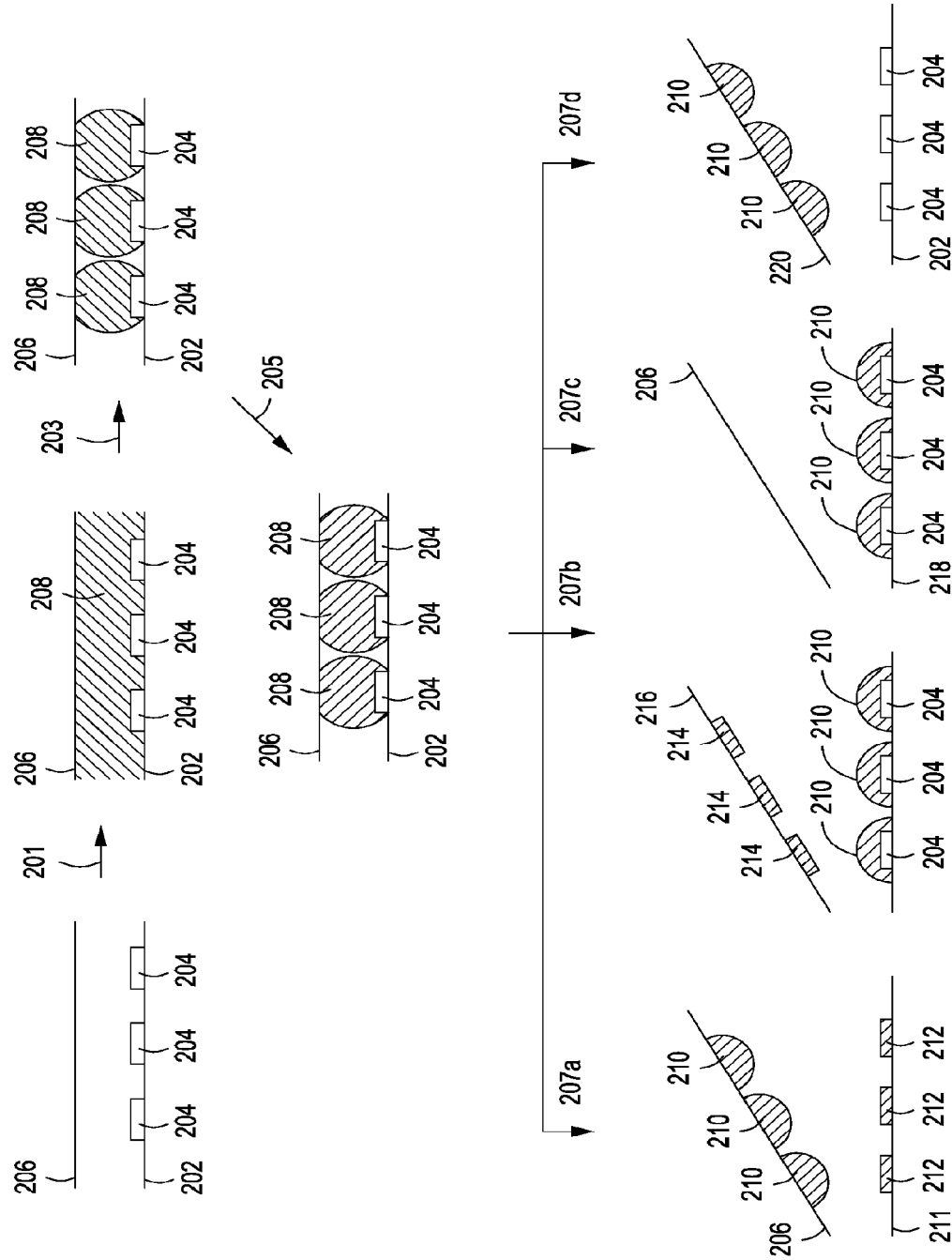
FIG. 2 illustrates exemplary methods for creating arrays of partitioned reaction products using a template array and one or more partitioning arrays, according to the invention.

FIG. 2 illustrates exemplary methods for creating arrays of partitioned reaction products using template array and one or more partitioning arrays, according to the invention. In FIG. 2, at least one of the template array or substrate shown comprises partitioning features and both may comprise partitioning features.

FIG. 2 shows a template array at 202 and a substrate at 206. Template array 202 comprises template molecules 204. At step 201, substrate 206 is brought into proximity with the template array 202 and a reaction mix 208 is provided in the space between the template array 202 and substrate 206. At step 203, reaction mix is partitioned in the space between template array 202 and substrate 206 by the partitioning features provided on at least one of the template array 202 and substrate 206, and at step 205, template molecules 204 and reaction mix 208 react to form a mixture of products and depleted reaction mix 210. In steps 207a-207d, the template and substrate are separated and the fate of the products in the partitioned volumes depends on the nature of the template array and the substrate, specifically whether either comprises capture moieties capable of binding the products in the partitioned reaction volumes, and which of the template array and substrate retains the partitioned volumes.

Four exemplary outcomes are illustrated but others are possible. In the leftmost branch of the figure, 207a, the template array comprises capture moieties which capture a portion of the products 212 while the substrate retains the partitioned mixture 210. The template array has been converted into a product array to be used as a research or diagnostic tool and the substrate subsequently may be used as a master substrate in, e.g., the methods described supra, using the rest of the products that were not captured by the template array. In the second branch, 207b, the substrate comprises capture moieties, which capture a portion of the products 214 and the template array retains the partitioned mixture 210. Thus, the substrate may be used as a research or diagnostic tool and the template array may be used as a master substrate. In the third branch, 207c, neither the template array or substrate contains capture moieties and the template array retains the partitioned mixture, thus the template array may be used as a master substrate. Finally in the rightmost branch, 207d, neither the template array nor the substrate contains capture moieties and the partitioned volumes are retained on the substrate, thus the substrate may be used as a master substrate.

Template molecules 204 may comprise, e.g., nucleic acids, proteins, peptides, small molecules, phage, cells and the like; the reaction mix 208 may comprise reaction components for PCR, transcription reactions, RT-PCR, translation reactions, or transcription reactions coupled with translation reactions, or enzymes, catalysts, antibodies or other reactants; and the products in mixture 210 may comprise DNA, mRNA, cDNA, mRNA-peptide hybrids or peptides or functionalized peptides. For example, if the template molecule is DNA and the reaction mix comprises components for PCR, the products will be DNA. In another example, if the template molecule is mRNA and the reaction mix comprises components for cell-free translation, the products will be peptides. In yet another example, if the template molecules are DNA and the reaction mix comprises components for transcription coupled with translation, the products will be mRNA-peptide hybrids or peptides.

As should be clear given the description herein, various permutations and combinations of template molecules, first reaction mixes, first products, second and subsequent reaction mixes, second and subsequent products and capture moieties may be used. The products to be printed and arrayed may be nucleic acids (e.g., DNA, cDNA, oligonucleotides, RNA, mRNA, miRNAs, etc.), peptides (proteins, functionalized peptides, enzymes, antibodies, antigens, etc.) or virtually any other molecule, cell, phage or the like capable of being and desired to be configured in an array format.

Methods for producing a template array comprising template molecules are well known in the art. For example, almost any technique for the generation of oligonucleotide arrays can be used, including but not limited to, production of arrays using the Affymetrix GeneChip technology (Affymetrix, Santa Clara, Calif.), including techniques disclosed in U.S. Pat. Nos. 7,736,906, 7,691,330, 7,547,775, 5,744,305, 5,677,195, 5,143,854 and U.S. Pat. Appln. Nos. 20100305006 and 20090192050; Agilent microarray technologies (Agilent Technologies, Inc., Santa Clara, Calif.), including but not limited to techniques disclosed in U.S. Pat. Nos. 7,642,097, 7,588,889, 656,740; 6,613,893; 6,599,693; 6,589,739; 6,587,579; 6,420,180; 6,387,636; 6,309,875; 6,232,072; 6,221,653; and 6,180,351 and U.S. Ser. No. 20060078889; Illumina microarray technology (Illumina, Inc., San Diego, Calif.), including but not limited to synthesis techniques disclosed in U.S. Pat. Nos. 6,942,968, 6,858,394, 6,770,441, 6,429,027; and other synthesis techniques such as those disclosed in U.S. Pat. Nos. 5,807,522, 5,700,637 and 5,445,934 and US Appln No. 20040259146.

The manufacturing and printing methods described herein are particularly useful for making peptide arrays by in vitro translation, using nucleic acid microarrays as the template array and using substrates, partitioning arrays and replica arrays to, e.g., partition the reactions, deliver reaction reagents, partition products and print replica arrays. In standard translation reactions, purified RNA is used as a template for translation, and the methods of the invention can be performed using mRNAs arrayed on the template array or in sequential methods with DNA arrayed on the template array, and mRNA as a first product. "Linked" or "coupled" systems, on the other hand, use DNA as a template and DNA is arrayed on the template array. In these systems, RNA is transcribed from the DNA and subsequently translated in a coupled reaction. Such systems typically combine a prokaryotic phage RNA polymerase and promoter (T7, T3, or SP6) with eukaryotic or prokaryotic extracts to synthesize proteins from exogenous DNA templates. The "linked" system may be performed as a two-step reaction, based on transcription with a bacteriophage polymerase followed by translation in rabbit reticulocyte or wheat germ lysate. If the transcription and translation reactions are separate, each can be optimized to ensure that both are functioning at full potential. Conversely, the methods of the invention preferably employ coupled transcription:translation reactions.

If the final products to be arrayed on replica arrays are peptides and a DNA microarray is used as a template array and are used to transcribe mRNAs that are used to generate the peptide products, the oligonucleotides on the template array preferably comprise a promoter region and a ribosome binding site (RBS) to enable translation. Optional sequences may be included as well, such as a sequence coding for an N-terminal common peptide (for example, a TEV protease site for labeling as described in Tolbert and Wong, Agnew. Chem. Int. Ed., 41(12):2171-74 (2001)) at the 5'-end of the peptide coding sequence, and/or sequences coding for a C-terminal common peptide tag (for example, an affinity tag for purification), as well as other sequences such as a sequence available for ligation of an adaptor moiety at the 3'-end. Adaptor moieties comprising a C-terminus binding moiety such as those described in, e.g., U.S. Pat. No. 6,416, 950 to Lohse and Kurz, et al., Chembiochem, 2:666-672 (2001), both of which are incorporated herein in their entirety, may be used in some embodiments of the methods of the invention.

Peptide array fabrication by in vitro translation techniques include protein in situ array (PISA) production (He and Taussig, Nucleic Acids Res., 29: e73 (2001)), nucleic acid programmable protein array (NAPPA) production (Ranachandran, et al., Science, 305:86-90 (2004)), DNA to protein array (DAPA) construction (He, Nat. Methods, 5:175-177 (2008), and arraying of proteins using in situ puromycin capture (Tao and Zhu, Nat. Biotech, 24:1253-1254 (2006)). In preferred embodiments, peptide constructs and assay systems described in Chee and Kozlov, PCT/US2010/44134, filed Aug. 2, 2010; Chee and Kozlov, PCT/US2010/59327, filed Dec. 7, 2010; and Chee and Kozlov, U.S. Ser. No. 61/473,709, filed Apr. 8, 2011 are used.

Alternatively, the template array may comprise peptide arrays manufactured by spotting pre-synthesized peptides on the substrate surface (Salisbury, et al, J. Am. Chem. Soc. 124(50):14868-70 (2002)) or by synthesizing peptides in spots using standard solid phase peptide synthesis (see, e.g., Frank, J. Immunol. Methods, 267(1):13-26 (2002)), or by employing other methods that enable direct chemical synthesis of peptides in microarray format (see, e.g., Antohe and Cooley, Methods Mol. Biol., 381:299-312 (2007)). The arrayed peptides may then be used as templates in the methods of the invention.

As described, the replica arrays of the invention comprise chemical and/or biochemical capture moieties—typically, one element of a binding pair—that is used to capture the products made when template molecules react with the reaction mix(es) of the invention. The capture moieties of the invention include nucleic acid capture moieties such as partially complementary strands for hybridization or splint ligation, DNA binding proteins or metalloproteins, or biotin or aldehyde labeled primers, for example.

Peptide capture moieties used to capture peptide products in some embodiments of the invention include antibody-antigen binding pairs. Alternatively, the peptide products of the invention may be modified to include one entity of a binding pair where the peptide capture agent comprises the other entity of a binding pair. For example, the peptide could comprise biotin, and the peptide capture moieties could comprise short streptavidin binding peptides such as StrepTag (see, e.g., Schmidt, et al., J. Mol. Bio., 255:753-66 (1996); Schmidt and Skerra, J. Chromatog. A., 676:337-345 (1994); and Skerra and Schmidt, Meth. in Enz., 326:271-304 (2000)), StrepTag II (see, e.g., Schmidt and Skerra, Nat. Protoc., 2:1528-35 (2007); and Voss and Skerra, Protein Eng., 10(8): 975-82 (1997)), or HPQ motifs (see, e.g., Gissel et al., J. of Peptide Science 1(4):217-226 (1995); and Helms et al., JBC, 282(13):9813-24 (2007)). Alternatively, oligo histidine peptide tags and His6 binding groups (see, e.g., Kneusel et al., Procedures for the Analysis and Purification of His-tagged Proteins, in Nucleic Acid Protocols Handbook, p. 921 (2000) (Humana Press); and Smith et al., Gene, 67:31-40 (1988)); or FLAG peptide tags and His6 or His5 peptide groups (see, e.g., Kozlov, Combinatorial Chemistry and High Throughput Screening, 11:24-35 (2008)); and the like may be employed with the peptide products and peptide capture moieties of the invention.

In yet another alternative, a chemically-reactive species (e.g., an aldehyde tag), label or other functionalized component may be added in the construction of the peptide products. For example, introduction of a sulfatase consensus sequence recognized by a formylglycine-generating enzyme results in site-specific introduction of aldehyde groups into the peptide products. The sulfatase consensus sequence can be between 6-13 amino acids in length, and the smallest such "aldehyde tags" are no larger than a His6 tag. Enzymatic modification at a sulfatase motif by formylglycine generating enzyme generates a formylglycine residue, which allows site-specific attachment of moieties that can be captured by a peptide capture moiety. This modification is reversible, and thus the introduction of this tag into the peptide constructs allows aldehyde-tagged peptides to be reversibly modified with multiple epitopes. Examples of aldehyde tags for use in the present invention are described in, e.g., US2008/0187956; Dierks and Frese, Chem. BioChem., 10:425-27 (2009); Wu, et al., "Site-specific chemical modification of recombinant proteins produced in mammalian cells by using the genetically encoded aldehyde tag," PNAS, cgi_doi_10.1073_pnas.807820106 (2009); Rush and Bertozzi, J. Am. Chem. Soc., 9:130:37, (2008); Landgrebe et al., Gene, 316: 47-56 (2003); Carrico, Nat. Chem. Biology, 3:6 (2007), each of which is incorporated by reference in its entirety for teaching useful tags and their use in peptide modification. Additionally, N-terminal formyl-methionine that is generated during translation initiation on all peptides can be specifically cleaved from the peptides by peptide deformylase and methionine aminopeptidase to expose the N-terminal cysteine. The resulting N-terminal cysteine residue can be used for peptide modification with an affinity residue (e.g., a biotin residue).

Also, in some embodiments, the master substrate may comprise capture moieties, where the products from the reaction with the template array are captured by capture moieties on the master substrate before they are printed or copies onto replica arrays. The printing or copying process would encompass releasing the products from the capture moieties on the master substrate by heat denaturing, photo-cleavage, pH change and the like. However, in preferred embodiments, the master substrate does not comprise capture moieties, and the products are partitioned on the master substrate in droplets as described in detail herein.

Since many biological reactions are temperature dependent, in some embodiments controlling the temperature during the manufacture and printing of the substrates is important. For example, in preferred embodiments, the processing temperature is kept low while the master substrate is being assembled, then the processing temperature is raised when reactions, such as DNA amplification, transcription, translation or other enzymatic processes, need to take place. Moreover, temperature control is one method to minimize evaporation of the template molecules, reaction mixes and products, particularly as very small volumes and feature sizes may be employed. Other methods for minimizing evaporation are described infra.

Exemplary Reaction Partitioning Methods

A key feature of the array manufacturing methods described is an array of partitioned reaction volumes on a substrate created using surface energetic barriers. There are many methods that can be used produce an array of partitioned volumes. In the most simple embodiment, a drop-on-demand or ink jet method can be used to deposit template molecules or reaction mix(es) into the features on a partitioning array. This method can also be useful if different reaction mixes are to be used in different features. In preferred embodiments the same reaction mix is deposited in all the partitioning features, so the features can be filled in parallel by, e.g., laminar flow, condensation of vapor or submerging the partitioned substrate in liquid and removing the excess liquid by wiping or spinning the partitioning array, or by evaporation.

Figure 3A:
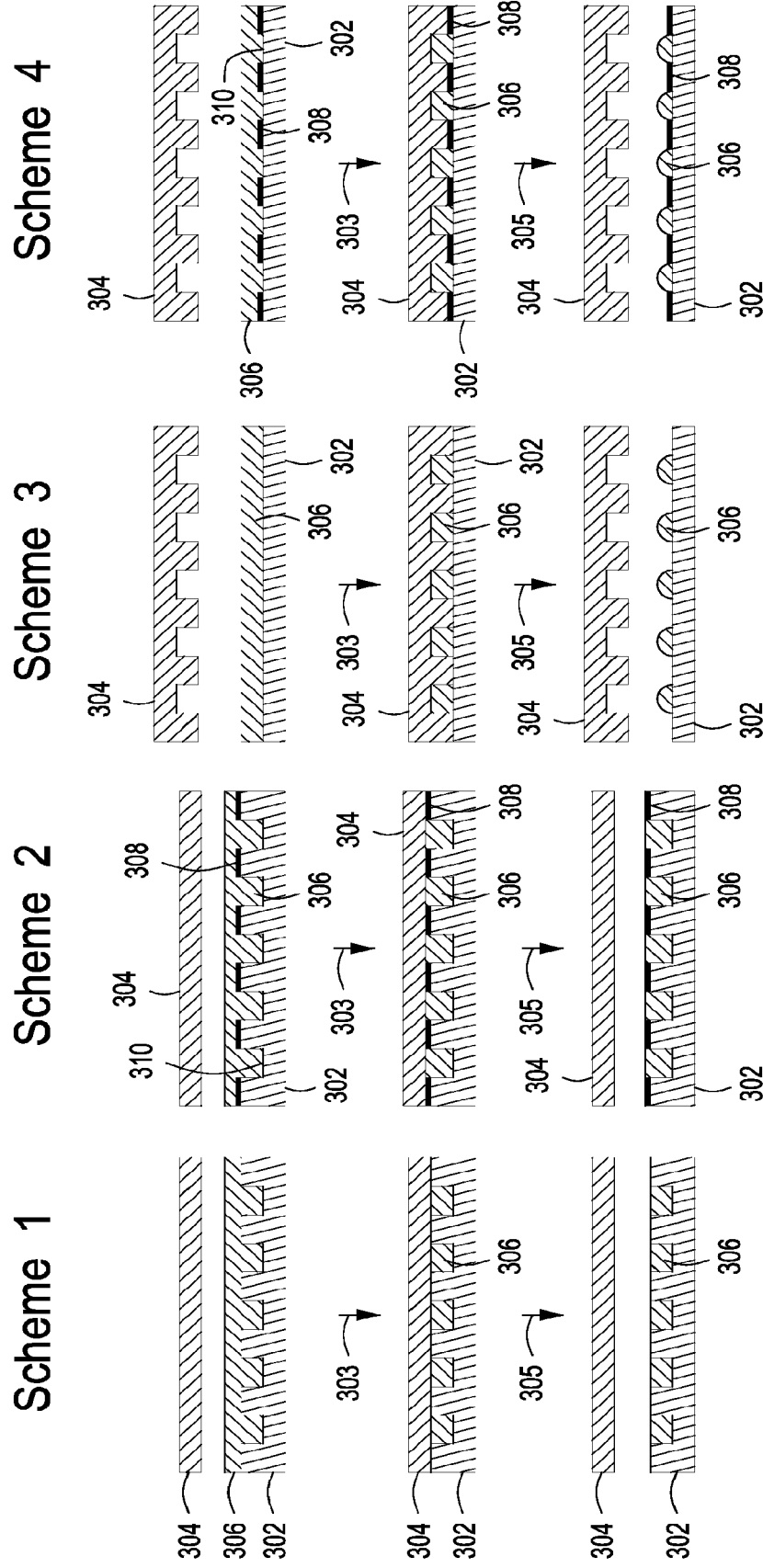
FIGS. 3A and 3B illustrate exemplary methods for creating arrays of partitioned reaction volumes using various types of partitioning arrays, according to the invention.

As an alternative to drop-on-demand or ink jet printing, partitioned reactions may be formed by contact or proximity between two substrates, where one or both of the substrates are partitioning substrates. Examples for manufacturing partitioning substrates are described infra. FIG. 3A shows four alternative embodiments using contact between two substrates, at least one of which is a partitioning substrate. In contact assembly, a reaction mix is added between surfaces of a partitioning array and a substrate, where the contact is sufficient to expel excess reaction mix from the interstices. The physical barriers alone separate the reaction mix (and thus the reactions) into partitioned reaction volumes; however, in order to be able to print many copies of the products from a master substrate to replica arrays, it is necessary that the partitioned reaction volumes containing the products be stable after one of the substrates is removed. Engineering the surface of the partitioning array and other substrates, e.g., as described in the next section by configuring slightly, moderately or very hydrophilic or hydrophobic regions on the substrates (creating surface energetic barriers) is one method that may be employed.

In Scheme 1 of FIG. 3A, liquid 306 is applied to a partitioning array 302, where the wells of the partitioning array 302 are moderately to very hydrophilic. A moderately to very hydrophobic unpartitioned substrate 304 is then brought into contact with partitioning array 302 at step 303, forcing the excess liquid out from between the partitioning array 302 and the unpartitioned substrate 304. At step 305, the partitioning array 302 and unpartitioned substrate 304 are separated, with the liquid 306 remaining partitioned in the hydrophilic wells of partitioning array 302.

In Scheme 2 of FIG. 3A, liquid 306 is applied to a partitioning array 302, where the wells 310 of the partitioning array 302 are moderately to very hydrophilic, and the interstices 308 of the partitioning array 302 are moderately to very hydrophobic. A moderately to very hydrophobic unpartitioned substrate 304 is then brought into contact with partitioning array 302 at step 303, forcing the excess liquid out from between the partitioning array 302 and the unpartitioned substrate 304. At step 305, the partitioning array 302 and unpartitioned substrate 304 are separated, with the liquid 306 remaining partitioned in the hydrophilic wells 310 of partitioning array 302.

In Scheme 3 of FIG. 3A, liquid 306 is applied to an unpartitioned slightly hydrophilic substrate 302. A moderately to very hydrophobic partitioning array 304 is then brought into contact with unpartitioned substrate 302 at step 303, forcing the excess liquid out from between the unpartitioned substrate 302 and the partitioning array 304. At step 305, the unpartitioned substrate 302 and partitioning array 304 are separated, with the liquid 306 remaining partitioned on the weakly hydrophilic surface of the unpartitioned substrate 302.

In Scheme 4 of FIG. 3A, liquid 306 is applied to a partitioning array 302, having hydrophilic virtual well regions 310 and hydrophobic interstices 308 forming surface energetic barriers between the wells. A moderately to very hydrophobic partitioning array 404 is then brought into contact with partitioning array 302 at step 303, forcing the excess liquid out from between partitioning array 302 and partitioning array 304. Note that the use of two partitioning arrays 302 and 304 requires that these arrays must be appropriately aligned. Alignment of substrates (partitioning and non-partitioning) can be achieved by methods and apparatus known in the art, such as tools similar to a contact lithography mask alignment tool and the like and as described in more detail infra. At step 305, partitioning array 302 and partitioning array 304 are separated, with the liquid 306 remaining partitioned in the hydrophilic virtual wells of partitioning array 302.

FIG. 3A thus shows four exemplary methods of contact assembly of arrays of partitioned reaction volumes using various configurations of hydrophobic and hydrophilic regions as well as physical barriers (i.e., various combinations of surface energetic barriers or features) to form partitioning features. However, other characteristics such as well depth, diameter, pitch and the like may be varied to create or enhance the properties of the surface energetic barriers; thus, many other combinations of these characteristics may be employed as appropriate. For example, another contact method may employ a substrate with wells that extend through an entire thickness of the substrate—so that the substrate is essentially perforated—and where flat substrates would be brought into contact with the perforated substrate, forcing excess reaction mix out, with the remaining reaction mix disposed within the perforations. Each perforation would then represent a partitioned reaction volume.

Figure 3B:
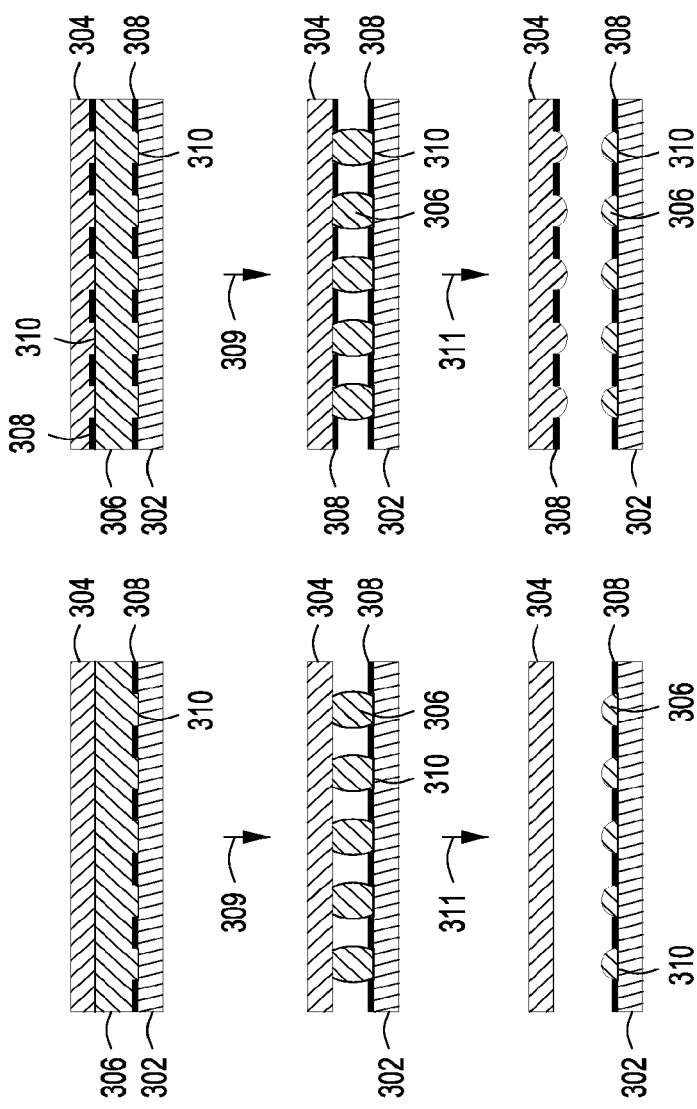

FIG. 3B shows three exemplary embodiments for partitioning a reaction between two proximal substrates at least one of which is a partitioning array. In Scheme 1 of FIG. 3B, liquid 306 is delivered to the space between a partitioning array 302 and a dummy substrate 304, where the wells 310 of the partitioning array 302 are moderately to very hydrophilic and the interstices 308 of the partitioning array 302 are moderately to very hydrophobic. The unpartitioned dummy substrate 304 is moderately to very hydrophobic. When dummy substrate 304 is brought into proximity with partitioning array 302 at step 309, the reaction mix is split into partitioned reaction volumes. This step can be aided by rapidly flowing the reaction mix into the gap between the proximal substrates, or by using air pressure or vacuum to displace excess reaction mixture. At step 311, the partitioning array 302 and unpartitioned substrate 304 are separated, with the liquid 306 remaining partitioned in the hydrophilic wells 310 of partitioning array 302.

In Scheme 2 of FIG. 3B, liquid 306 is delivered between a partitioning array 302, having moderately to very hydrophilic virtual wells and very hydrophobic interstices 308, and a moderately to very hydrophobic unpartitioned substrate 304. The unpartitioned substrate 304 is then brought into proximity with partitioning array 302 at step 309, and the reaction mix is partitioned. Again, this may be aided by rapidly flowing the reaction mix into the gap between the proximal substrates, or by using air pressure or vacuum to displace excess reaction mixture. At step 311, the partitioning array 302 and unpartitioned substrate 304 are separated, with the liquid 306 remaining partitioned in the hydrophilic virtual wells 310 of partitioning array 302.

In Scheme 3 of FIG. 3B, liquid 306 is delivered between a partitioning array 302, having moderately to very hydrophilic virtual wells and very hydrophobic interstices 308, and a second partitioning array 304, also having moderately to very hydrophilic virtual wells and very hydrophobic interstices 308. The partitioning arrays 302 and 304 are then brought into proximity with proper alignment, and the reaction mix is partitioned. Again, partitioning be aided by rapidly flowing the reaction mix into the gap between the proximal substrates, or by using air pressure or vacuum to displace excess reaction mixture. At step 311, the partitioning arrays 302 and 304 are separated, with the liquid 306 remaining in the hydrophilic wells 310 of both partitioned substrates 302 and 304. The amount of liquid remaining on each substrated is determined by the geometry and surface properties of the wells on each substrate. As with the embodiments for contact assembly shown in FIG. 3A, the embodiments of proximity assembly shown in FIG. 3B are only exemplary partitioning schemes. Many other schemes, making use of combinations of surface properties and well depth, pitch, shape, etc., may be employed as appropriate.

Reaction mix volumes on the substrates may vary from 10 µl to 1 fL. Reaction mix volumes and products in microliter to femtoliter volumes present a challenge due to evaporation of the reaction mix or products. The challenge may be overcome by decreasing the temperature during manufacture and printing of the arrays (i.e., during non-reaction times); alternatively or in addition, processing may be performed in a vapor-saturated environment such as a humidified glovebox.

An additional approach for stabilizing the reaction mixes and products is to add a hydrogel-forming polymer to the reaction mixes. The hydrogel can be cooled to solidify or gel after manufacture and during transfer of substrates, but can be liquefied when the temperature is increased in order for reactions to occur. Solidifying the partitioned reaction volumes decreases the evaporation rate and generally protects the integrity of the drops during processing and handling of the substrates. Generally, solidifying reaction products on a master substrate between replica array printings helps to stabilize the products. One exemplary hydrogel useful in this embodiment of the invention is an ultra-low gelling temperature agarose such as Agarose Type IX from Sigma-Aldrich Corp. (St. Louis, Mo.), which has a gelling temperature below room temperature and a melting temperature of approximately 50° C., compatible with many biochemical or enzymatic reactions. In addition, use of a hydrogel provides the further advantage of enabling electrophoretic transfer of reaction products from a master substrate to replica arrays, thus facilitating the printing of the replica arrays.

Partitioning Arrays

A key feature of the invention is the partitioning of biochemical reactions into arrays of discrete reaction volumes. Partitioning refers to spatially separating the biochemical reactions into partitioned reaction volumes of microliters to femtoliters to avoid mixing of reactants or products by, e.g., diffusion, convection or turbulent mixing. In the simplest embodiment, partitioned reaction volumes are formed by depositing isolated reaction volumes at an adequate spacing to prevent merging or mixing; alternatively, in preferred embodiments the partitioning is effected by the use of one or more partitioning arrays as described in relation to FIG. 1A through 1D and as further described below. Such partitioning arrays comprise wells surrounded by barriers, where the combination of well and barrier forms a partitioning feature. Features can comprise physical wells and barriers (e.g., depressions surrounded by ridges), or they can be virtual wells, where the feature comprises and area of low surface energy surrounded by a high surface energy barrier (e.g., a hydrophilic spot surrounded by a hydrophobic ring). Partitioning features can be formed using a combination of physical and surface energetic elements and a partitioning array may have both physical and virtual features.

Partitioning arrays—like non-partitioning arrays—may consist of any of a variety of materials including glass, silicon wafers, silicone rubber, thermoplastics, and the like. The surface properties of partitioning arrays (and in some embodiments, non-partitioning arrays) are altered by chemical or physical modification and/or thin-film deposition to create the partitioning features. In some preferred embodiments, such processes are used to create a pattern of many highly-hydrophilic regions surrounded by highly hydrophobic regions. In the description of the present invention, it is assumed that reaction mixes and solvents are aqueous and thus substrate regions are described as hydrophilic or hydrophobic; however, the methods of the invention can be adapted to nonpolar, fluorous or other liquids by changing the surface treatment of the relevant substrate.

Figure 4A:
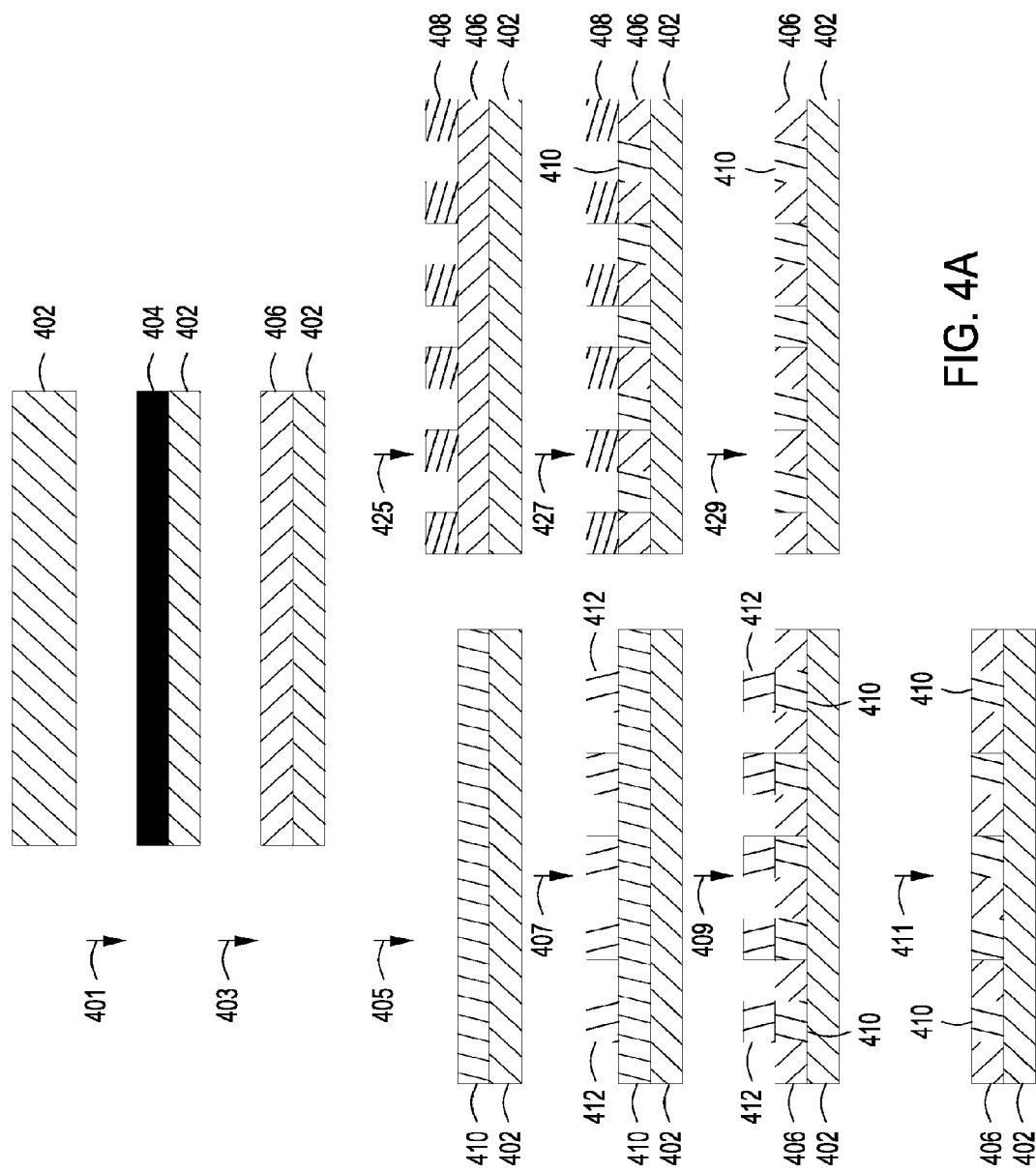
FIGS. 4A and 4B illustrate methods of manufacturing exemplary partitioning arrays that may be used in the methods of the invention.
Figure 4B:
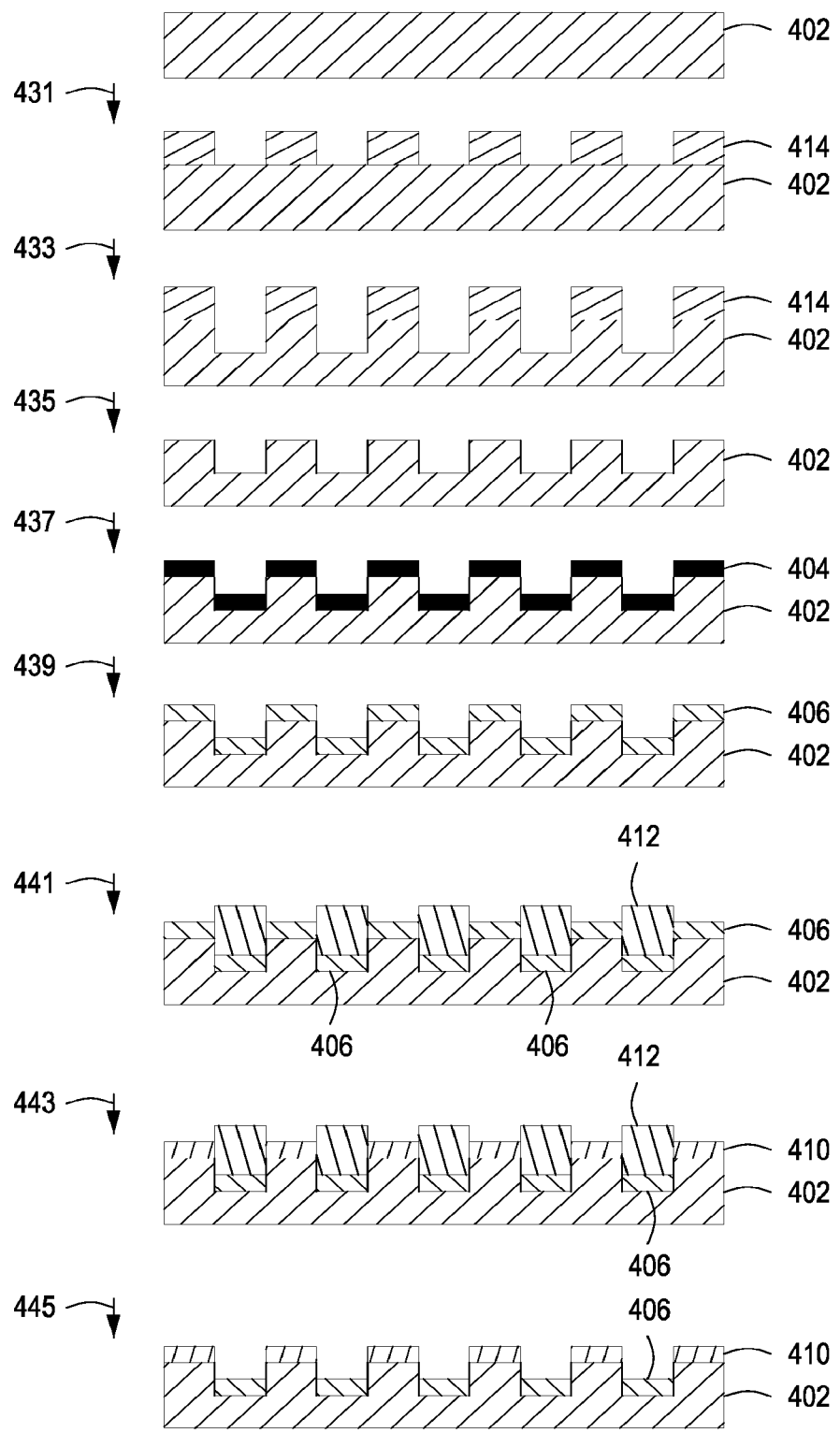

Preferred embodiments provide partitioning arrays with patterning created on a micro- to nanometer scale. FIGS. 4A and 4B illustrate exemplary methods for manufacturing preferred embodiments of partitioning arrays. In a preferred embodiment, silicon is used for the partitioning array due to the availability of plasma etching processes that may be used to produce highly-hydrophilic and highly-hydrophobic nanostructured surfaces. Single crystal silicon wafers may be used if opaque substrates are acceptable, or glass or quartz wafers with chemical vapor deposition (CVD) deposited silicon films may be used if transparent substrates are preferred. Techniques well known to those skilled in the art of microfabrication are employed; for example, chemical vapor deposition, physical vapor deposition, and etch processes combined with UV-lithographic patterning permits creation of partitioning arrays with partitioning features as small as one micron. In other embodiments, nanostuctured patterns may also be transferred to other transparent substrates such as glass or plastic substrates by techniques including replica-casting, hot-embossing, nanoimprint-lithography to produce transparent partitioning arrays if required.

FIG. 4A shows two alternatives for manufacturing partitioning arrays where the partitioning features are surface energetic wells formed by patterning of highly-hydrophilic and highly-hydrophobic materials. A silicon wafer is shown at 402. In step 401, silicon wafer 402 is subjected to a deep reactive ion etch (DRIE) process such as a cryo-etch or Bosch-etch process to produce nanoscale pyramid or needle-like features of black silicon 404 on the silicon wafer 402. At step 403, the black silicon is chemically modified by oxidation in a furnace, oxygen plasma system or by plasma enhanced CVD (PECVD) deposition of silicon oxide to produce a superhydrophilic surface. Looking at the left branch of FIG. 4A, at step 405, the oxidized black silicon is coated with a thin film of fluoropolymer 410 by, e.g., plasma deposition, to yield a superhydrophobic surface. At step 407, a photoresist 412 is deposited and lithographically patterned to allow selective etching of fluoropolymer 410. At step 409, an oxygen plasma is used to etch the exposed fluoropolymer 410 to expose the oxidized black silicon 406. Note that the photoresist 412 is much thicker than the fluoropolymer layer so it is largely preserved despite some loss of thickness due to etching. Finally, at step 411 the photoresist 412 is removed to expose the fluoropolymer-coated oxidized black silicon 410 (i.e., superhydrophobic regions) adjacent to oxidized black silicon 406 (i.e., superhydrophilic regions). Thus, adjacent superhydrophilic and superhydrophobic regions on a micrometer scale are produced.

Looking at the right branch of FIG. 4A, in step 401, silicon wafer 402 is subjected to a deep reactive ion etch (DRIE) process to produce nanoscale pyramid or needle-like features of black silicon 404 on the silicon wafer 402. At step 403, the black silicon is chemically modified by oxidation in a furnace, oxygen plasma system or by plasma enhanced CVD (PECVD) deposition of silicon oxide to product a superhydrophilic surface. At step 425, a photoresist 408 is deposited in a desired pattern to allow for lithographic patterning of the oxidized black silicon 406 by the process known as "liftoff" by those skilled in the art. Step 427 involves plasma deposition of a fluoropolymer 410 on the exposed areas of the oxidized black silicon 406 as well as on top of the patterned photoresist. At step 429, the photoresist 408 is removed, exposing the regions of oxidized black silicon 406 (i.e., superhydrophilic regions) adjacent to regions of fluoropolymer coated black silicon 410 (i.e., superhydrophilic regions).

FIG. 4B shows an alternative method for manufacturing a partitioning array where the partitioning features consist of both physical and "virtual" elements. Physical depressions are etched into a silicon substrate that is subsequently modified to yield surface energetic wells (hydrophilic surfaces) and surface energetic barriers (hydrophobic surfaces) aligned with the physical wells. Partitioning of substrates with physical wells allows more control over the volume of each reaction partition than use of virtual wells only. At step 431, a silicon wafer 402 is patterned with photoresist 414. At step 433, areas of the silicon wafer 402 not protected with photoresist 414 are etched to produce wells of the desired depth. At step 435, photoresist 414 is removed, and at step 437, DRIE is performed to generate black silicon 404. At step 439, surface oxidation 406 of the black silicon is performed, and at step 441, a photoresist 412 is deposited and patterned to protect the wells of silicon wafer 402. At step 443, a fluoropolymer 410 is deposited on the silicon wafer, and at step 445 liftoff of the photoresist 412 is performed to expose the oxidized black silicon 406 (i.e., superhydrophilic regions) adjacent to regions of fluoropolymer coated black silicon 410 (i.e., superhydrophilic regions).

It should be noted that there are many methods available in the art to produce superhydrophobic and superhydrophilic (surface energetic) surfaces including, but not limited to direct patterning by electron-beam lithography and plasma etching, replication by nano-imprint lithography or soft lithography, or deposition of material by chemical-vapor deposition, sputtering or sol-gel processes. Partitioning arrays may be formed by these methods as well as others, and the exemplary methods shown are but a few.

In the methods of the invention, the size of the various substrates including master substrates, template arrays, partitioning arrays and capture arrays may range from 1 mm to 1000 mm, or 1 mm to 300 mm, or 10 mm to 150 mm, or 25 mm to 75 mm. In preferred embodiments each of the substrates (i.e. master and capture, or partitioning and template) will be the same size and have the same number of features. In other embodiments, one or more of the substrates may be differently sized or not all of the features on each substrate may be used. Partitioning feature sizes may range from 1 mm to 100 nm, or 1 mm to 1 μm, or 100 μm to 1 μm, or 100 μm to 10 μm, with partition volumes ranging from 10 μL to 1 fL, or 1 μL to 100 fL, or 1 μL to 1 pL, or 100 pL to 10 pL. Template features may be smaller, equally sized or larger than the corresponding partitioning features as the partitioned reaction volumes can completely cover the template feature, or a portion may extend outside the partition. Product feature size is determined by the area of the interface of the partitioned reaction volume and the capture moiety-bearing surface, be it the partitioning array or a replica array. In preferred embodiments the product features are approximately the same size as the partitioning features. Center-to-center distances between partitioning features, or "pitch" can range from 10 mm to 100 nm, or 1 mm to 1 μm, or 100 μm to 1 μm, or 100 μm to 10 μm. In preferred embodiments, template features, and thus product features have the same pitch as the partitioning features. Partitioning feature, template feature and product feature density may range from 0.01 features per mm$^2$ to 50 features per μm$^2$, 1 feature per mm$^2$ to 1 feature per μm$^2$, 10 features per μm$^2$ to 0.1 features per μm$^2$, or 100 features per mm$^2$ to 10,000 features per mm$^2$. Exemplary designs of product arrays produced by the methods described include quartz, silicon or float-glass microarray slide format substrate (25 mm×75 mm×1 mm) with 100,000 distinct protein features. The size of each feature is 50 um and the pitch of the features is 100 um. A second example is a 6" silicon wafer patterned with 10 million protein features with a 20 um feature size and 40 um pitch.

Printing Replica Arrays

Figure 5:
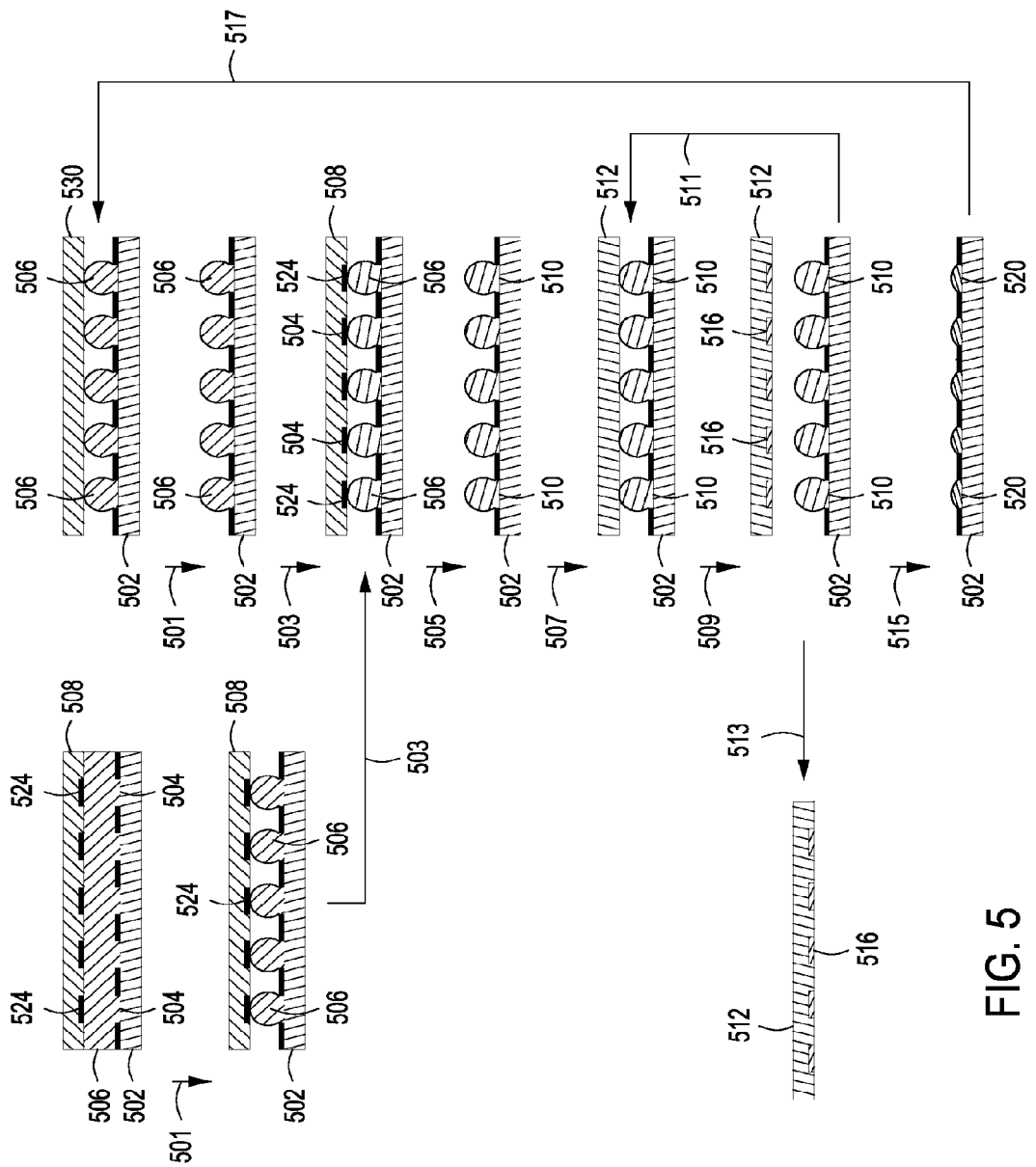
FIG. 5 illustrates an exemplary method for manufacturing many replica arrays from a single template array according to the invention.

FIG. 5 illustrates an exemplary method for manufacturing many replica arrays according to the invention. The left and right sides represent two different exemplary methods. In FIG. 5 on the lefthand side, a partitioning array 502 with virtual wells 504 is brought into proximity with a template array 508 with template molecules 524, with reaction mix 506 delivered into the space between the partitioning array 502 and template array 508. At step 501, the reaction mix is partitioned and excess is removed from between the partitioning array 502 and template array 508. At step 503, the template molecules 524 disposed on template array 508 are allowed to react with the partitioned reaction mix 506.

In FIG. 5, on the righthand side, a partitioning array 502 with virtual wells is brought into proximity with an unpartitioned substrate 530, with reaction mix 506 delivered into the space between the partitioning array 502 and substrate 530. Substrate 530 acts as a dummy substrate providing a surface to allow reaction mix 506 to be partitioned on partitioning array 502. At step 501, dummy substrate 530 is removed, leaving reaction mix partitioned on the partitioning array 502. Template array 508 comprising template molecules 524 is brought into proximity with the partitioning array 502, where the template molecules 524 disposed on the template array 508 are allowed to react 503 with the reaction mix 506. Note that the lefthand and righthand sides of FIG. 5 use slightly different methods, yet arrive at the same point.

At step 505, the template array 508 is removed, preserving partitioned volumes of depleted reaction mix containing products 510 on partitioning array 502, which now may act as a master substrate for printing one or more replica arrays. After removal, the template array 508 can be re-used as a source of template molecules to be brought into proximity with yet another substrate (as here, a partitioning array). At step 507, a replica array 512 comprising capture moieties is brought into proximity with the partitioning array 502 (now master substrate 502), where products in the partitioned volumes 510 on the master substrate 502 can be captured by capture moieties on the replica array 512. The partitioning array (now master substrate 502), is used to print or stamp out replica arrays. Replica array 512 is brought into proximity with master substrate 502, contacting partitioned volumes 510 in a manner that preserves the integrity of the partitioned volumes 510 while allowing the capture of products by the capture moieties on the replica array 512. The proximity between replica array 512 and master substrate 502 is maintained for a period of time sufficient to allow the immobilization of a desired fraction of products from the partitioned volumes 510 on replica array 512.

At step 509, the master substrate 502 comprising partitioned volumes 510 and the replica array 512 comprising captured products 516 are separated. At this point, the replica array 512 can be used at step 513 as a research or diagnostic tool using captured products 516, and the master substrate 502 with partitioned volumes 510 can be used at step 511 to copy or print more replica array 512 comprising capture moieties, until at step 515 products are depleted (shown as depleted partitions 520 on partitioning array 502). The number of replica arrays that can be printed or copied from a single master substrate depends on the volume of products, the size of the features, and the like, but as many as 2, 5, 10, 25, 50, 100, 250, 500, 750, 850, 900 or 1000 or more replica arrays may be printed from a single master substrate without having to replenish the master substrate with additional reactions and products. For example, the PURExpress kit (New England Biolabs) typically yields up to 200 µg peptide per mL of reaction mix. For a partitioned reaction with cylindrical partitions of 60 um diameter and 60 um height, this corresponds to 3.4e-11 grams of peptide per partition or 1.7e-14 moles of 16-mer peptide per partition. Also as an example, a surface functionalized with closely packed IgG molecules, each capable of capturing 1-2 peptide molecules depending on its orientation with respect to the surface, will have an areal density of ~1.2e-11 moles per square cm, capable of capturing 2.8-5.6e-16 moles of peptide per spot. Thus each partition in this example could produce enough peptide to completely functionalize 25-50 spots of equal area so each partitioned reaction can produce 25-50 replica arrays. The partitioning array 502 (master substrate) comprising depleted products 520 can be re-used in the process at step 517.

Looking at FIG. 5, it should be clear that various permutations and combinations of partitioned and unpartitioned substrates (template arrays, dummy substrates, partitioning arrays, replica arrays, etc.), comprising template molecules, reaction mixes, and capture moieties may be used in the methods of the invention. One skilled in the art given the teachings of this specification regarding the partitioning, hydrophobicity and hydrophilicity of the various substrates, potential template molecules, reaction mixes, products, and the final character of the desired arrayed biomolecule products should be able to design several to many schemes to achieve a desired array.

Figure 6:
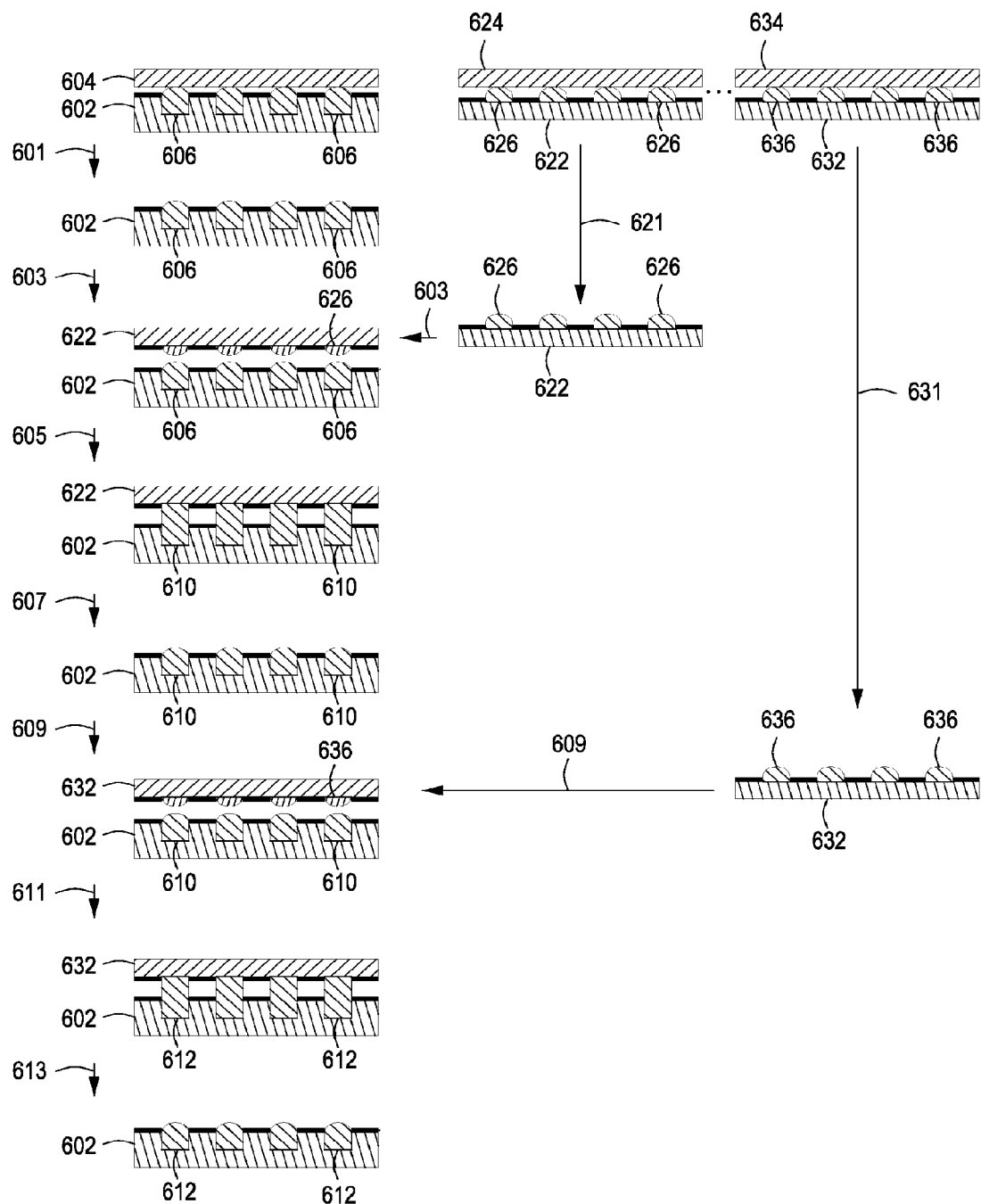
FIG. 6 illustrates an exemplary combinatorial method for manufacturing and molecular arrays according to the invention.

FIG. 6 illustrates an exemplary combinatorial method for manufacturing molecular arrays according to the invention. Combinatorial methods, in the sense demonstrated in FIG. 6, allow for a sequential addition of template molecules, reagents, reactants, catalysts, members of binding pairs, capture moieties, and the like. First partitioning array 602 is shown comprising reaction mix 606 between first partitioning array 602 and a substrate 604. As seen previously, substrate 604 simply acts as a dummy substrate allowing reaction mix 606 to be properly partitioned within the wells of a first partitioning array 602. FIG. 6 also shows a second partitioning array 622 and a second dummy substrate 624 with a second reaction mix 626 disposed between them. At steps 601 and 621, dummy substrates 604 and 624 are removed, and at step 603 the first partitioning array 602 and second partitioning array 622 comprising reaction mixes 606 and 626, respectively, are brought into proximity. At step 605, the first and second reaction mixes are allowed to merge or combine into combined reaction mix 610, and at step 607, the second partitioning array 622 is removed, leaving first partitioning array 602 comprising combined reaction mix 610. In some embodiments such as the one shown here, virtual wells of varying hydrophobic and hydrophilic character or physical wells of varying depth may be used to ensure that the bulk of the combined reaction mix 610 remains on the desired (here, first) partitioning array.

FIG. 6 further shows a third partitioning array 632 and a third dummy substrate 634 with a third reaction mix 636 disposed between them. At step 631, dummy substrate 634 is removed, and at step 609 the first partitioning array 602 comprising combined reaction mix 610 and the third partitioning array 632 comprising third reaction mix 636 are brought into proximity. At step 611 reaction mixes 610 and 636 are allowed to combine and react to produce combined reaction mix 612 (now comprising three different reaction mixes), and at step 613 first partitioning array 602 and third partitioning array 632 are separated, leaving combined reaction mix 612 disposed on first partitioning array 602. This process can be repeated with additional substrates until the desired reaction mixes and products are introduced and produced.

Again, it should be apparent to one skilled in the art given the teachings herein that the sequential nature of the method shown in FIG. 6 lends itself to delivery of different template molecules, reaction components, reagents, reactants, capture moieties, catalysts and the like as needed to produce products to be arrayed. Any one of the first, second, third, etc., partitioning arrays in this example could be template arrays, capture substrates, or substrates used to deliver reaction components or simply used to aid in partitioning reaction mixes, etc. Also, it should be noted that conditions may be provided to react reaction components on the first partitioning array at any point in the process shown; that is, conditions may be provided after every delivery of reaction components to the first partitioning array, or at one or more but not all deliveries of reaction components to the first partitioning array.

Further, in yet another embodiment, the character of partitioned reaction volumes may be engineered so that components of a droplet may combine with another droplet, but the droplet solvent does not; such as, for example, using immiscible compounds for the droplets with favorable partitioning coefficients. Such a process would allow, e.g., reagent delivery or reagent extraction from a reaction mix.

Figure 7:
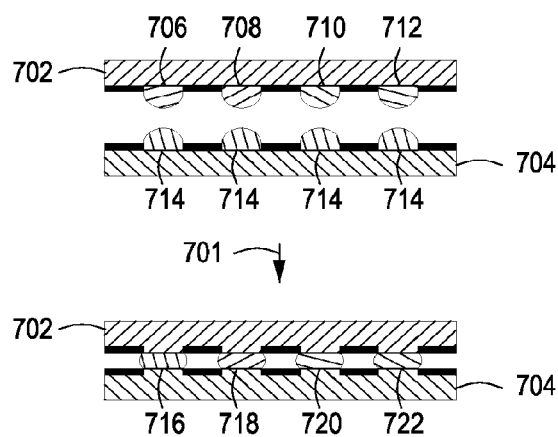
FIG. 7 is a simplified illustration of another combinatorial configuration that may be used in methods of the invention.
Figure 7:
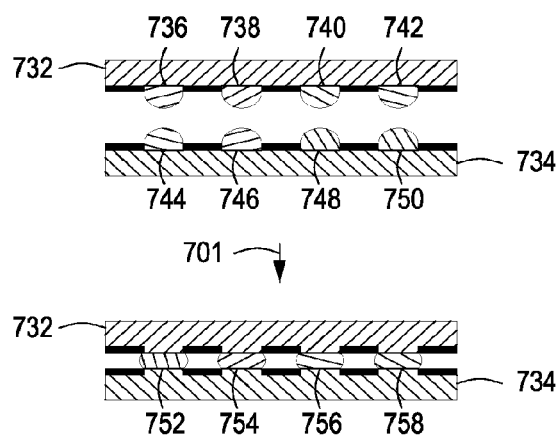

FIG. 7 is a simplified illustration of another combinatorial configuration that may be used in methods of the invention. In Scheme 1 of FIG. 7, an array of partitioned volumes 702 comprising different reaction components 706, 708, 710 and 712 is brought into proximity at step 701 with substrate 704 comprising partitioned volumes of a reaction mix 714, where the combined components and reaction mix react to form products 716, 718, 720 and 722. However, in Scheme 2 of FIG. 7, an array of partitioned volumes 732 comprising different reaction components 736, 738, 740 and 742 is brought into proximity at step 701 with substrate 734 comprising partitioned volumes of different reaction mixes 744, 746, 748 and 750, where the combined different components and different reaction mixes react to form products 716, 718, 720 and 722. Thus, the methods of the invention can be used to perform different reactions using a pair of partitioning array by customizing the contents of the partitioned volumes on either or both of the arrays.

Figure 8:
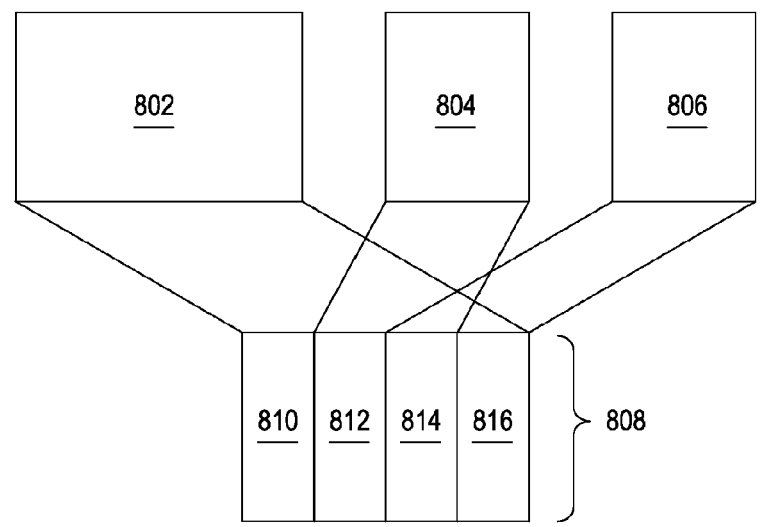
FIG. 8 shows in a simplified manner yet another combinatorial configuration that may be employed in manufacturing molecular arrays.

FIG. 8 illustrates yet another variation of a combinatorial approach that can be used with the methods of the invention. FIG. 8 shows a first partitioning substrate 802, a second partitioning substrate 804 and a third partitioning substrate 806. The first, second and third substrates are different sizes or can be oriented differently to deliver different, specific reagents or template molecules to specific regions of a substrate. For example, substrate 808 has four different regions: 810, 812, 814 and 816. Region 810 comprises components from first substrate 802 only. Region 812 comprises components from first substrate 810, second substrate 804 and third substrate 806. Region 184 comprises components from first substrate 802 and second substrate 804, and region 816 comprises components from first substrate 802 and third substrate 806.

A reagent delivery system useful in methods of the invention may include instrumentation that allows the delivery of reagents to discrete regions or features on the substrates.

Reagent delivery systems useful in methods of the invention may comprise imaging means, reagent delivery hardware and control software. Reagent delivery can be achieved in a number of different ways. Technologies for formulating and delivering both biological molecules and chemical reagents are known in the art, and uses of these instrument systems are known to one skilled in the art and easily adaptable to the methods of the invention. One example of a suitable reagent delivery system is the Labcyte™ Echo acoustic liquid handler, which can be used to deliver nanoliter scale droplets containing biological molecules and reagents with high precision and reproducibility. The Labcyte™ Echo reagent delivery device may be integrated into an overall system, using software to specify the locations to which reagents should be delivered.

Other instruments that may be used for the deposition of template molecules and reagents onto biological samples include, but are not limited to, ink jet spotting; mechanical spotting by means of pin, pen or capillary; micro-contact printing; photochemical or photolithographic methods (some of which have been described supra); and the like. For several applications, it may be preferred to segment or sequester certain areas of the substrates into one or more assay areas for different reagent distribution and/or biological target determination. The assay areas may be physically separated using barriers or channels.

In one exemplary aspect, the reagent delivery system may be a flow-based system. Flow-based systems for reagent delivery for use in the invention may include instrumentation such as one or more pumps, valves, fluid reservoirs, channels, and/or reagent storage cells. Reagent delivery systems are configured to move fluid to contact a discrete section of the substrates. Movement of the reagents can be driven by a pump disposed, for example, downstream of the fluid reagents. The pump can drive each fluid reagent to (and past) the reaction compartment. Alternatively, reagents may be driven through the reaction compartment by gravity. US Pub. Nos. 20070166725 and 20050239192 disclose certain general-purpose fluidics tools that can be used with the methods of the invention, allowing for the precise manipulation of gases, liquids and solids to accomplish very complex analytical manipulations with relatively simple hardware.

In a more specific example, one or more flow-cells can be attached to a substrate from above. The flow-cell can include inlet and outlet tubes connected thereto and optionally an external pump is used to deliver reagents to the flow-cell and across the substrate. If desired, the flow cells may be configured to deliver reagents only to certain portions of the substrate, restricting the amount and type of reagent delivered to any specific section of the substrate. In another alternative, a microfluidic system can be integrated into the substrate or externally attached on top of the substrate. Microfluidic passages for holding and carrying fluid may be formed on and/or above the planar substrate by a fluidics layer abutted to the substrate. Fluid reagents can be selected and delivered according to selective opening and closing of valves disposed between reagent reservoirs.

Pumps generally include any device for moving fluid and/or reagents disposed in fluid. In some examples, the pump can be configured to move fluid and/or reagents through passages with small volumes (i.e., microfluidic structures). The pump can operate mechanically by exerting a positive or negative pressure on fluid and/or on a structure carrying fluid, electrically by appropriate application of an electric field(s), or both, among other means. Exemplary mechanical pumps may include syringe pumps, peristaltic pumps, rotary pumps, pressurized gas, pipettors, etc. Mechanical pumps may be micromachined, molded, etc. Exemplary electrical pumps may include electrodes and may operate by electrophoresis, electroendoosmosis, electrocapillarity, dielectrophoresis (including traveling wave forms thereof), and/or the like.

Valves generally include any mechanism for regulating the passage of fluid through a channel. Valves can include, for example, deformable members that can be selectively deformed to partially or completely close a channel, a movable projection that can be selectively extended into a channel to partially or completely block a channel, an electrocapillary structure, and/or the like.

An open gasket can be attached to the top of the substrate and reagents can be injected into the gasket. Suitable gasket materials include, but are not limited to, neoprene, nitrile, and silicone rubber. Alternatively, a watertight reaction chamber may be formed by a gasket sandwiched between the substrate and a chemically inert, water resistant material such as, but not limited to, black-anodized aluminum, thermoplastics (e.g., polystyrene, polycarbonate, etc), glass, etc.

In an optional embodiment, instrumentation employed in the methods of the invention comprises imaging means to determine features and organization of the products on the replica arrays. If included, the delivery system can comprise a microcircuit arrangement including an imager, such as a CCD or IGFET-based (e.g., CMOS-based) imager and an ultrasonic sprayer for reagent delivery such as described in US Pub. No. 20090197326, which is incorporated herein by reference.

In yet another alternative, a delivery system may deliver reagents to specific patterns on a substrate surface using semiconductor techniques such as masking and spraying. Specific areas on the substrate surface can be protected from exposure to reagents through use of a mask to protect specific areas from exposure. Reagents may be introduced to the substrate using conventional techniques such as spraying or fluid flow. The use of masked delivery results in a patterned delivery scheme on the substrate surface. In an alternative embodiment, reagent delivery instrumentation may be based on ink-jet printing technology. There are a variety of different ink-jetting mechanisms (e.g., thermal, piezoelectric). Sets of independently actuated nozzles can be used to deliver multiple reagents at the same time, and very high resolutions are be achieved.

In many embodiments of the invention—particularly those where feature sizes and interstices are small—mechanisms to register and align very precisely the substrate for reagent delivery, two substrates to combine reagents, and/or the master substrate to the replica arrays for printing are thus important components of the instrumentation used with the invention. Mechanisms such as the use of fiducial markers on slides and/or other very accurate physical positioning systems can be adapted to this purpose.

Instrumentation for use with the invention preferably comprises a suite of software tailored to the array manufacturing and printing system. Optionally, oligonucleotide design software is used to design template molecules for the specific assay to be run, and may be integrated as a part of the system. Also optionally, algorithms and software for reagent delivery and data analysis (i.e., sequence analysis) may be integrated into a useful system. Integrated data analysis is particularly useful, as the type of dataset that is generated may be massive as a consequence of scale. Algorithms and software tools that are specifically designed for analysis of spatially-associated data, including pattern-analysis software and visualization tools, may enhance the value of the data.

In certain aspects, the methods employ a system that provides processes for making and carrying out the quality control of reagents, e.g., the integrity and sequence fidelity of oligonucleotides, reagents, and the like. In particular, reagents are formulated according to factors such as volatility, stability at key temperatures, and chemical compatibility for compatibility with the reagent delivery instrumentation and may be analyzed by instrumentation integrated within the assay system.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Partitioning Array Fabrication

A partitioning array was fabricated from a standard silicon wafer. First, a patterned gasket comprising a boundary region surrounding the area to contain partitioning features was formed on the wafer by using UV lithography to pattern a 20 μm-thick layer of SU-8 epoxy-based negative photoresist on the wafer. The gasket was formed such that the partitioning array, when brought into proximity with another substrate (a dummy substrate, template array or capture substrate or replica array, for example), would form a flowcell. The wafer was then baked at 300° C. to make the SU-8 substantially impervious to subsequent processing. The wafer was then cryo-etched using reactive-ion etching with inductively coupled plasma (RIE/ICP) at negative 140° C. using $SF_6$ and $O_2$ to form black silicon. The black silicon consisted of conical pillars, approximately 2 μm high and 100-200 nm wide.

A conformal layer of silicon dioxide approximately 50-200 nm in thickness was then deposited on the wafer by plasma-enhanced chemical vapor deposition, causing the black silicon layer to be superhydrophilic. The water contact angle was found to be less than 5 degrees. The silicon dioxide layer also served as a spacer layer to mitigate quenching of fluorescence from fluorescent labels that may be immobilized on the surface of the wafer. The wafer was then coated with a fluoropolymer layer, which was patterned by liftoff. Positive photoresist was patterned by UV-lithography to produce an array of circular resist features surrounded by open areas. The fluoropolymer was deposited by plasma-assisted deposition of $C_4F_8$ gas in an RIE/ICP system at room temperature. The fluoropolymer coated the black silicon pillars with a conformal layer approximately 5-50 nm thick to yield a superhydrophobic surface. This surface exhibited an advancing water contact angle of >170 degrees. The circular photoresist features protected the underlying black silicon and preserved the superhydrophilic nature of the features once this photoresist was removed by washing in solvents. An additional coating of photoresist was applied to the wafer to protect it during mechanical processing. The wafer was cut with a diamond saw into individual chips and two holes were drilled in each chip with a diamond drill to provide fluid ports once the chips were assembled into flowcells with partitioning arrays. Prior to use, the photoresist protective coating was removed with solvents and the chip was dried and baked.

Example 2

Capture Substrate Fabrication

A borofloat glass microscope slide was used to prepare the capture substrate. First, the slides were cleaned using solvents and a strong acid/oxidizer bath, and were then cleaned further using a UV-Ozone cleaner (Jelight, Inc., Irvine, Calif.). The slides were functionalized using (3-aminopropyl)tri-methozysilane (APTMS) in a vapor deposition system at 150° C. and 3 torr for 10 minutes. Amine functionality on the capture substrate (chip) was confirmed by labeling with Lissamine Rhomdamine B Sulfonyl Chloride, an amine-reactive fluorescent dye, and imaging with a microarray scanner.

Example 3

Capture Substrate Printing

The flowcell was assembled by bringing the silicon partitioning array into contact with the capture substrate so that the SU-8 gasket surrounding the region of partitioning features contacted the edges of the capture substrate and the black silicon surface of the partitioning array was held at a distance equal to the thickness of the gasket. The partitioning array and capture substrate were then clamped together, and a tube was connected to the output port of the flowcell, where the output port was formed by one of the holes drilled into the partitioning array. The tube was then connected to a vacuum source.

A small volume of buffer containing reactive molecules, in this case fluorescein isothiocyanate (FITC), was pipetted into the input port formed by the second hole drilled into the partitioning array, where the FITC was pulled through the flow cell by the vacuum. The entire volume of the flow-cell was filled temporarily while the buffer transited the flowcell. Most of the buffer exited the flowcell through the output port; however, droplets of FITC-containing buffer solution remained adhered to each the hydrophilic features of the partitioning array and spanned the height of the flowcell to contact the capture array as well. The vacuum was disconnected, the ports were sealed, and the assembly was incubated at room temperature in the dark for one hour to allow the FITC to react with the amine groups on the capture substrate.

After one hour, the vacuum line was reconnected and several aliquots of wash buffer were pipetted into the input port, flushing the partitioning array and capture substrate thereby washing unbound molecules from the surface of the capture substrate. The flowcell was then disassembled (that is, the partitioning substrate and capture substrate were separated), and the capture substrate was rinsed and dried. Fluorescent imaging revealed that the surface of the capture substrate was patterned corresponding to the partitions on the partitioning array, where each feature showed up as a fluorescent spot. There was no discernible mixing between spots, as evidenced by the lack of fluorescence in the interstitial regions of the capture substrate (data not shown).

Example 4

Synthetic Oligonucleotide Array to Peptide Array Conversion Using Partitioned Reaction The ability to achieve peptide arrays of high density was demonstrated by converting DNA arrays using in situ coupled translation and transcription in a partitioned reaction. Partitioning allowed for feature densities much greater than methods previously described in the art.

DNA Array Preparation:

Single-stranded oligonucleotide templates encoding peptide sequences of interest were synthesized at individual features on the surface of a microarray bearing surface energetic barriers in the form of hydrophilic spots surrounded by hydrophobic interstitial regions. Using methods known in the art, many DNA templates may be synthesized in parallel. Each of the templates had universal oligo sequences at the 5' and 3' ends. A universal sequence was used for attachment of a universal untranslated DNA region linked to a group capable of peptide capture. The universal oligo sequence at the 3' end coded for an affinity tag and a stop codon. A sequence coding for a peptide of interest was located between the universal oligo sequences at the 5' and 3' ends. A third universal DNA sequence containing an untranslated region (UTR) with a T7 promoter and a ribosomal binding site (RBS) was attached to each template, and a universal primer complementary to the universal oligo sequence at the 3' end was annealed to each template. Double-stranded DNA was formed via extension of this universal primer by DNA polymerase. A capture group was introduced at the end of one of the DNA strands on the array.

Conversion to Peptide Array:

The DNA array was assembled in a flow-cell configuration to allow a small volume of reagent to be presented to the surface in a laminar flow modality. Energetic barriers were employed on the DNA array in addition to an extremely low-energy opposing surface which forced the coupled transcription/translation (TNT) mixture to be split into partitioned reaction volumes where the footprint of each partition corresponded to the area of a single DNA feature. The double stranded oligonucleotides formed on the array surface were used as templates for the in vitro coupled transcription/translation reaction. After the flow-cell was filled with TNT mixture (PURExpress, NEB, Ipswich, Mass.) and the mixture was partitioned, the flow-cell was incubated at 37° C. for 30 minutes. The reaction resulted in encoded peptides fused to an affinity tag at their C-terminus that was bound to the capture group on the DNA array, generating of an array of peptides attached to their own DNA templates.

By employing a partitioned reaction with only one template species per partition, the diffusion of products between features was prevented and it was demonstrated that the density of features can be increased dramatically above that of peptide arrays currently used in the art. Here, a template with 60 μm diameter DNA features with a spacing of 15 μm between the edges of adjacent features was used. The DNA features that encoded the peptides and served as templates for the peptide features were surrounded by non-encoding features that were capable only of capturing the products via the affinity tag (capture-only features). In most cases there was no discernible level of peptide products on the capture-only features as the products were constrained to the encoding features by the energetic barriers. Thus, the size of the product features was equal to the size of the DNA features, 60 μm. Using the described methods, a peptide array with a density of >21,500 features per square centimeters can be achieved. The total number of features is only limited by the starting oligonucleotide array. Current DNA array technology allows approximately 1 million features per 2.5 cm×7.5 cm array.

The preceding merely illustrates the principles of the invention. It will be appreciated that those skilled in the art will be able to devise various array manufacturing and printing arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. §112, ¶6.

I claim:

1. A method of manufacturing an array of products on a replica array comprising:
   delivering a continuous volume of a liquid reagent or reaction mix on the surface of a master substrate by laminar flow;
   providing partitioned reaction volumes of the liquid reagent or reaction mix on the master substrate, wherein the reaction volumes are partitioned by surface energetic barriers provided by adjacent hydrophobic regions and hydrophilic regions on the master substrate;
   generating products by one or more enzymatic processes in the partitioned reaction volumes of the liquid reagent or reaction mix; and
   immobilizing the products from the partitioned reaction volumes from the master substrate on capture moieties disposed on a replica array that is in contact with the partitioned reaction volumes, wherein partitioning of the reaction volumes prevents diffusion of products between them.

2. The method of claim 1, wherein the reaction volumes are partitioned by surface energetic barriers on the master substrate.

3. The method of claim 1, wherein the master substrate is a template array.

4. The method of claim 1, wherein there are at least 100 partitioned reaction volumes per square centimeter on the master substrate.

5. The method of claim 4, wherein there are at least 10,000 partitioned reaction volumes per square centimeter on the master substrate.

6. The method of claim 1, wherein at least 1000 different products from separate partitioned reaction volumes on the master substrate are arrayed on the replica array at a density of at least 1000 different products per square centimeter.

7. The method of claim 1, wherein at least a portion of each product from substantially all partitioned reaction volumes are arrayed on the replica array.

8. The method of claim 1, further comprising after the immobilizing step, the steps of
removing the replica array;
sequentially furnishing to the master substrate one or more replica arrays comprising capture moieties; and
immobilizing the products from the partitioned reaction volumes from the master substrate on the capture moieties on the one or more replica arrays, wherein partitioning between products from separate partitioned reaction volumes is preserved.

9. The method of claim 1, further comprising after the immobilizing step, the steps of:
replenishing or regenerating partitioned reaction volumes on the master substrate;
generating products by one or more enzymatic processes in the partitioned reaction volumes on the master substrate;
sequentially furnishing to the master substrate one or more replica arrays comprising capture moieties; and
immobilizing the products from the partitioned reaction volumes from the master substrate on the capture moieties on the one or more replica arrays, wherein partitioning between products from separate partitioned reaction volumes is preserved.

10. The method of claim 1, wherein at least one component of at least one of the enzymatic process is attached to the master substrate.

11. The method of claim 1, wherein the one or more enzymatic processes comprise one or more of replication, transcription, and translation.

12. The method of claim 1, wherein the reaction volumes are partitioned by surface energetic barriers on the replica array.

13. The method of claim 1, wherein the reaction volumes are partitioned by the combination of surface energetic barriers on the master substrate and surface energetic barriers on the replica array.

14. The method of claim 1, wherein the surface energetic barriers are provided by adjacent superhydrophobic regions and hydrophilic regions on the master substrate.

15. The method of claim 1, wherein physical barriers are provided to partition the reaction volumes, wherein the physical barriers are provided on the master substrate or on the replica array, or by a combination of the master substrate and the replica array.

16. The method of claim 1, wherein the partitioned reaction volumes in the providing step contain one or more enzymes.

17. The method of claim 1, wherein excess liquid reagent or reaction mix during partitioning in the providing step is removed by wiping or spinning the master substrate, by evaporation, or by using air pressure or vacuum.

18. The method of claim 1, wherein the surface energetic barriers are provided by adjacent superhydrophobic regions and superhydrophilic regions on the master substrate.

* * * * *